(12) United States Patent
Van Straten et al.

(10) Patent No.: US 7,994,189 B2
(45) Date of Patent: *Aug. 9, 2011

(54) DIHYDROPYRIDINE DERIVATIVES

(75) Inventors: Nicole Corine Renee Van Straten, Oss (NL); Gerritdina Geziena Gerritsma, Oss (NL); Lars Anders Van Der Veen, Vienna (NL)

(73) Assignee: N.V. Organon, Oss (NL)

( * ) Notice: Subject to any disclaimer, the term of this patent is extended or adjusted under 35 U.S.C. 154(b) by 78 days.

This patent is subject to a terminal disclaimer.

(21) Appl. No.: 11/912,719

(22) PCT Filed: May 4, 2005

(86) PCT No.: PCT/EP2005/052042
§ 371 (c)(1),
(2), (4) Date: Jan. 28, 2008

(87) PCT Pub. No.: WO2006/117023
PCT Pub. Date: Nov. 9, 2006

(65) Prior Publication Data
US 2009/0215773 A1      Aug. 27, 2009

(51) Int. Cl.
A61K 31/44        (2006.01)
A61K 31/47        (2006.01)

(52) U.S. Cl. ............... 514/297; 514/311; 514/314

(58) Field of Classification Search .......... 14/311, 14/314, 297; 514/311, 314, 297
See application file for complete search history.

(56) References Cited

U.S. PATENT DOCUMENTS

| 6,087,503 | A | 7/2000 | Furuya et al. |
| 6,194,428 | B1 | 2/2001 | Urbahns et al. |
| 2008/0262033 | A1 | 10/2008 | Karstens et al. |
| 2008/0275042 | A1 | 11/2008 | Poveda et al. |
| 2008/0300270 | A1 | 12/2008 | Timmers et al. |

FOREIGN PATENT DOCUMENTS

| DE | 1070162 | 12/1959 |
| EP | 0 755 931 | 1/1997 |
| JP | 2003026630 | 1/2003 |
| WO | WO 94/08966 | 4/1994 |
| WO | WO 96/06610 | 3/1996 |
| WO | WO 00/08015 | 2/2000 |
| WO | WO 00/78768 | 12/2000 |
| WO | WO 02/09706 | 2/2002 |
| WO | WO 03/004028 | 1/2003 |
| WO | WO 2004/056779 | 7/2004 |

OTHER PUBLICATIONS

Altmayer, et al., "Propofol Binding to Human Blood Proteins", *Arzneim.-Forsch./Drug Res.* (1995) 45: 1053-1056.
Anelli et al., "Smiles Rearrangement as a Tool for the Preparation of 5-[(2-Hydroxyacyl)amino]- 2,4,6-triiodo-1,3-benzenedicarboxamides: Main Pathway and Side Reactions," *Tetrahedron* (1997) 53:11919-11928.

Aranyos, et al., "An Application of the Stille Coupling for the Preparation of Arylated Phthalonitriles and Phthalocyanines", *Acta Chem. Scand.* (1999) 53: 714-720.
Bahner, et al., "Halogenated Aminobenzaldehydes and Aminostyrylquinolines", *J. Org. Chem*, 25 (1960) 2053-2055.
Baker, William R. "Alkoxide-Accelerated Smiles Rearrangements. Synthesis of N-(2-Hydroxyethyl)anilines from N-(2-Hydroxyethyl)(aryloxy)acetamides," *J. Org. Chem.* (1983) 48: 5140-5143.
Bierbaum et al., "Hypotensive 1,2,4-Benzothiadiazines," *J. Med. Chem.* (1963) 6: 272-275.
Claiborne et al., "Orally Efficacious NR2B-Selective NMDA Receptor Antagonists," *Bioorg. & Med. Chem. Lett.* 13:697-700, 2003.
Crich, et.al., "Enantiospecific Synthesis with Amino Acids. Part 2. a-Alkylation of Tryptophan: A Chemical and Computational Investigation of Cyclic Tryptophan Tautomers", *J. Chem. Soc. Perkin Trans.* 2 (1992) 2233-2240.
Devroey, et al., "Successful in-vitro fertilisation and embryo transfer after treatment with recombinant human FSH", *Lancet* 339 (1992) 1170-1171.
Dondoni et al., "Two- and Three-Component Hantzsch Reaction Using C-Glycosylated Reagents. Approach to the Asymmetric Synthesis of 1,4-Diyhydropyridines", *Synlett* (2002) 89-92.
Dorrington & Armstrong, "Effects of FSH on Gonadal Functions", *Recent Prog. Horm. Res.*, 35 (1979) 301-342.

(Continued)

*Primary Examiner* — San-Ming Hui
(74) *Attorney, Agent, or Firm* — Patricia A. Shatynski; Valerie J. Camara

(57) ABSTRACT

The present invention relates to dihydropyridine derivatives having general formula (I) or a pharmaceutically acceptable salt thereof, wherein $R^1$ is (1-6C)alkyl, (2-6C)alkenyl, (2-6C)alkynyl, phenyl, (1-5C)heteroaryl $R^2$, $R^3$ are independently (1-4C)alkyl, (2-4C)alkenyl, (2-4C)alkynyl, (1-4C)alkoxy, (24C)alkenyloxy, (2-4C)alkynyloxy, halogen X is $SO_2$, $CH_2$, C(O) or X is absent $R^4$ is (1-6C)alkyl, (2-6C)alkenyl, (2-6C)alkynyl, (3-6C)cycloalkyl, (3-6C)cycloalkenyl, (3-6C)cycloalkyl(1-4C)alkyl, (2-6C)heterocycloalkyl, (2-6C)heterocycloalkyl(14C)alkyl, (6-1 OC)aryl, (6-10C)aryl(1-4C)alkyl, (1-9C)heteroaryl or (1-9C)heteroaryl(14C)alkyl. The compounds are useful for the treatment of fertility disorders.

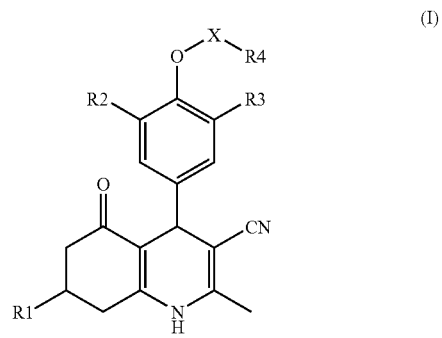

(I)

13 Claims, No Drawings

OTHER PUBLICATIONS

Dow, et al., "Discovery of a Novel Series of 6-Azauracil-Based Thyroid Hormone Receptor Ligands:Potent, TRβ Subtype-Selective Thyromimetics", *Bioorg. & Med. Chem. Lett.* 13 (2003) 379-382.

Drizin, et al., "Structure-Activity Studies for a Novel Series of Tricyclic Dihydropyrimidines as KATP Channel Openers (KCOs)", *Bioorg. & Med. Chem. Lett.* 12 (2002) 1481-1484.

Eisner, et al., "The Chemistry of Dihydropyridines", *Chem. Rev.* 72 (1972) 1-42.

Fisher, et al., "Heteroatom-Directed Metalation. Lithiation of N-Propenylbenzamides and N-Propenyl-o -toluamides. Novel Routes to Ortho-Substituted Primary Benzamide Derivatives and N-Unsubstituted Isoquinolin-1(2H)-ones", *J. Org. Chem.* 57 (1992) 2700-2705.

Fukuyama, et al., "2,4-Dinitrobenzenesulfonamides: A Simple and Practical Method for the Preparation of a Variety of Secondary Amines and Diamines", *Tetrahedron Lett.* 38 (1997) 5831-5834.

Greiner, A., "TDA-1 Catalysis in Smiles Rearrangement of N-Arylphenoxyamides. Accelerating Effect of the 2,4,6-Trichloro Substitution," *Tetrahedron Lett.* 30:931-934, 1989.

Guilford, et al., "Synthesis, Characterization, and Structure-Activity Relationships of Amidine-Substituted (Bis)benzylidene-Cycloketone Olefin Isomers as Potent and Selective Factor Xa Inhibitors," *J. Med. Chem.* 42:5415-5425, 1999.

Guo, et al., "Enantioselective Addition of Diethylzinc to Benzaldehyde Catalyzed by Chiral Titanate Complexes with Helical Ligands", *Tetrahedron* 53 (1997) 4145-4158.

Harvey, et al., "o-Nitroaniline Derivatives. Part 11. 4- and 7-Amino-IH-benzimidazole 3-Oxides", *J. Chem. Soc. Perkin Trans.* 1 (1988) 1939-1943.

Insler, V., "Gonadotropin Therapy: New Trends and Insights", *Int. J. Fertil.*, 33 (1988) 85-97.

Jia, et al., "Expression of Human Luteinizing Hormone (LH) Receptor: Interaction with LH and Chorionic Gonadotropin from Human but not Equine, Rat, and Ovine Species", *Mol. Endocrinol.* 5 (1991) 759-768.

Kansal, et al., "Diuretic Agents: Synthesis of 1,2-Disubstituted 7-Sulphamoylbenzimidazole-5-Carboxylic Acids," *Indian J. Chem.* 18B:88-90, 1979.

Katsumi, et al., "Studies on Styrene Derivatives. I. Synthesis and Antiinflammatory Activities of a-Benzylidene-γ-butyrolactone Derivatives", *Chem. Pharm. Bull.* 34 (1986) 121-129.

Kesten, et al., "Synthesis and Antimalarial Properties of 1-Imino Derivatives of 7-Chloro-3-substituted-3,4-dihydro-1,9(2H,10H)-acridinediones and Related Structures", *J. Med. Chem.* 35 (1992) 3429-3447.

Krohn, et al., "Total Synthesis of Angucyclines. Part 15: A Short Synthesis of (±)-6-Deoxybrasiliquinone B", *Tetrahedron* 56 (2000) 4753-4758.

Kuehne, et al., "1,4-Dihydrobenzoic Acid", *Org. Synth. Coll.* 5 (1973) 400.

Kumar, et al., "Synthesis and Evaluation of Anticancer Benzoxazoles and Benzimidazoles Related to UK-1", *Bioorg. & Med. Chem.* 10 (2002) 3997-4004.

Lal, et al., "Regiospecific Oxidation by DDQ Of Unhindered Alkyl Groups In Sterically Hindered Aromatic Amines", *Tetrahedron Lett.* 25 (1984) 2901-2904.

Langry, K.C., "Synthesis Of Imidazoquinolines And Imidazoisoquinolines From Azanaphthalene Carboxylic Acids", *Org. Prep. Proced. Int.* 26 (1994) 429-438.

Larget, et.al. "A Convenient Extension of the Wessely-Moser Rearrangement for the Synthesis of Substituted Alkylaminoflavones as Neuroprotective Agents In Vitro", *Bioorg. & Med. Chem. Lett.* 10 (2000) 835-838.

Lavilla, R., "Recent developments in the chemistry of dihydropyridines", *J. Chem. Soc., Perkin Trans.* 1 (2002) 1141-1156.

Loev, et al., "Hantzsch-Type Dihydropyridine Hypotensive Agents", *J. Med. Chem.* 17 (1974) 956-965.

Manchand, et al., "Synthesis of 3,4,5-Trimethoxybenzaldehyde", *Synth. Commun.* 20 (1990) 2659-2666.

Mariella, et al., "Synthesis of Some Aromatic Malononitriles", *J. Org. Chem.* 23 (1958) 120-121.

Mayer, et.al., "Über Carbocyclische Reduktone. Dihyrogpyogallol und Dihydrogallussäure", *Chem. Ber.* 88 (1955) 316-327.

McCarthy, et al., "Synthesis and Renal Vasodilator Activity of 2-Chlorodopamine and N-Substituted Derivatives," *J. Med. Chem.* 29: 1586-1590 (1986).

Miri, et al., "Synthesis and Calcium Channel Modulating Effects of Modified Hantzsch Nitrooxyalkyl 1,4-Dihydro-2,6-dimethyl-3-nitro-4-(pyridinyl or 2-trifluoromethylphenyl)-5-pyridinecarboxylates", *Drug Dev. Res.* 51 (2000) 225-232.

Mitchell, et al., "N-Bromosuccinimide-Dimethylformamide: A Mild, Selective Nuclear Monobromination Reagent for Reactive Aromatic Compounds", *J. Org. Chem.* 44 (1979) 4733-4735.

Morse, et al., "Hetrogeneity of Proteins in Commercial Preparations of Human Chorionic Gonadotropin (hCG) Demonstrated by Western Blotting", *Amer. J. Reproduct. Immunol. and Microbiology* 17 (1988) 134-140.

Navot, et al., "The Use of Follicle-Stimulating Hormone for Controlled Ovarian Hyperstimulation in In Vitro Fertilization",*J. In Vitro Fert. Embryo Transf.* 5 (1988) 3-13.

Nguyen, et al., "Hantzsch 1,4-Dihydropyridines Containing a Nitrooxyalkyl Ester Moiety to Study Calcium Channel Antagonist Structure—Activity Relationships and Nitric Oxide Release", *Drug Dev. Res.* 51 (2000) 233-243.

Nobel, D., "The Copper-Carbon Dioxide System, a New Mild and Selective Catalyst for the Methoxylation of Non-activated Aromatic Bromides", *J. Chem. Soc., Chem. Commun.* 4 (1993) 419-420.

Novak, et al, :Hydrolysis and $Fe^{2+}$-Induced Reduction of N-Aryl-O-pivaloylhydroxylamines: Aqueous Solution Chemistry of Model Carcinogens, *J. Org. Chem.* 53 (1988) 4762-4769.

Olijve, et al., "Molecular Biology and Biochemistry of Human Recombinant Follicle Stimulating Hormone (Puregon®)", *Mol. Hum. Reprod.* 2 (1996) 371-382.

Olson, et al., "A Dopamine Receptor Model and Its Application in the Design of a New Class of Rigid Pyrrolo[2,3-g]isoquinoline Antipsychotics", *J. Med. Chem.* 24 (1981) 1026-1034.

Raviña, et al., "Conformationally Constrained Butyrophenones with Affinity for Dopamine (D1, D2, D4) and Serotonin (5-HT2A, 5-HT2B, 5-HT2C) Receptors: Synthesis of Aminomethylbenzo[b]furanones and Their Evaluation as Antipsychotics", *J. Med. Chem.* 43 (2000) 4678-4693.

Sainani, et al., "Synthesis of 4-aryl-1,4,5,6,7,8-hexahydro-5-oxo-2,7,7-trimethylquinoline-3- carboxylates and amides", *Indian J. Chem.* 33B (1994) 526-531.

Sarma, et al., "Solid State Nuclear Bromination with N-Bromosuccinimide. Part 2. Experimental and theoretical studies of reactions with some substituted benzaldehydes", *J. Chem. Soc., Perkin Trans.* 2, (2000) 1119-1124.

Sarma, et al., "Solid State Nuclear Bromination with N-bromosuccinimide. Part 1. Experimental and theoretical studies on some substituted aniline, phenol and nitro aromatic compounds", *J. Chem. Soc., Perkin Trans.* 2, (2000) 1113-1118.

Shadyro et al, "Synthesis and Antiviral Activity of N-Acyl Derivatives of 4,6-Di-(*tert*-Butyl)-2-Aminophenol", *Pharm. Chem. J.*, 36 (2002) 410-412.

Sharma, et al., "Syntheses of Some Mannich Bases of Formyl & Other Substituted Phenols as Potential Spermicides", *Indian J. Chem.*, 20B (1981) 1010-1013.

Sharpe, R.M., "Intratesticular Control Of Steroidogenesis", *Clin. Endocrinol.*, 33 (1990) 787-807.

Shilcrat, et al., "A New Regioselective Synthesis of 1,2,5-Trisubstituted 1H-Imidazoles and Its Application to the Development of Eprosartan ," *J. Org. Chem.* 62:8449-8454, 1997.

Sircar, et al., "Calcium Channel Blocking and Positive Inotropic Activities of Ethyl 5-Cyano-1,4-dihydro-6-methyl-2-[(phenylsulfonyl)methyl]-4-aryl-3-pyridine-carboxylate and Analogues. Synthesis and Structure-Activity Relationships", *J. Med. Chem.*, 34 (1991) 2248-2260.

Stratowa, et al., "Use of a luciferase reporter system for characterizing G-protein-linked receptors", *Curr. Opin. Biotechnol.*, 6 (1995) 574-581.

Theilacker, et al.,"Zur Konstitution dér Triacylmethane. II. Über das Bicyclo-[2,2,2]-octantrion-(2,6,7)", *Justus Liebig's Annalen der Chemie*, 570 (1950) 15-33.

Turconi, et al., "Synthesis of a New Class of 2,3-Dihydro-2-oxo-1 H-benzimidazole-1-carboxylic Acid Derivatives as Highly Potent 5-HT3 Receptor Antagonists", *J. Med. Chem.*, 33 (1990) 2101-2108.
Vierhapper, et al., "Zur Sauerstoffoxidation von Kreosolderivaten in alkalisch-wäβriger Lösung", *Monatsh. Chem.*, 106 (1975) 1191-1201.
Visentin, et al. "Synthesis and Voltage-Clamp Studies of Methyl 1,4-Dihydro-2,6-dimethyl-5-nitro-4-(benzofurazanyl)pyridine-3-carboxylate Racemates and Enantiomers and of Their Benzofuroxanyl Analogues," *J. Med. Chem.*, 42 (1999) 1422-1427.
Vitolina, et al. "Synthesis and Study of the pharmacological activity of derivatives of condensed 1, 4-dihydropyridines," *Khimiko-Farmatsevticheskii Zhurnal*, 15 (1981) 39-42.
Wadia, et al., "A Convenient Preparation of N-Alkyl and N-Arylamines by Smiles Rearrangement—Synthesis of Analogues of Diclofenac," *Synth. Commun.*, 33:2725-2736, 2003.
White, et al., "Resistance-Modifying Agents. 9. Synthesis and Biological Properties of Benzimidazole Inhibitors of the DNA Repair Enzyme Poly(ADP-ribose) Polymerase", *J. Med. Chem.*, 43 (2000) 4084-4097.
Wong, et al., "Identification of a Dihydropyridine as a Potent α1a Adrenoceptor-Selective Antagonist That Inhibits Phenylephrine-Induced Contraction of the Human Prostate", *J. Med. Chem.*, 41 (1998) 2643-2650.
Yagupolskii, et al., "Vasorelaxation by New Hybrid Compounds Containing Dihydropyridine and Pinacidil-Like Moieties", *J. Med. Chem.*, 42 (1999) 5266-5271.

Database CAPLUS Chemical Abstracts Service, Columbus, Ohio, US; XP-002288485 retrieved from STN accession No. 1802 Database accession No. 1981:497547.
XP-002369583 Retrieved from STN, Database Registry [Online] RN:330674-72-1, Apr. 10, 2001.
Search Report issued on May 12, 2005 in connection with PCT Intl. Appln. No. PCT/EP2005/052042.
Written Opinion issued on Nov. 4, 2007 in connection with PCT Intl. Appln. No. PCT/EP2005/052042.
International Preliminary Report On Patentability issued on Nov. 6, 2007 in connection with PCT Intl. Appln. No. PCT/EP2005/052042.
Search Report issued on Aug. 18, 2006 in connection with PCT Intl. Appln. No. PCT/EP2006/061972.
Written Opinion issued on Nov. 4, 2007 in connection with PCT Intl. Appln. No. PCT/EP2006/061972.
International Preliminary Report on Patentability issued on Nov. 4, 2007 in connection with PCT Intl. Appln. No. PCT/EP2006/061972.
Search Report issued on Jul. 5, 2006 in connection with PCT Intl. Appln. No. PCT/EP2006/061976.
Written Opinion issued on Nov. 4, 2007 in connection with PCT Intl. Appln. No. PCT/EP2006/061976.
International Preliminary Report on Patentability issued on Nov. 4, 2007 in connection with PCT Intl. Appln. No. PCT/EP2006/061976.
Search Report issued on Jul. 5, 2006 in connection with PCT Intl. Appln. No. PCT/EP2006/061978.
Written Opinion issued on Nov. 4, 2007 in connection with PCT Intl. Appln. No. PCT/EP2006/061978.
International Preliminary Report on Patentability issued on Nov. 4, 2007 in connection with PCT Intl. Appln. No. PCT/EP2006/061978.

DIHYDROPYRIDINE DERIVATIVES

CROSS REFERENCE TO RELATED APPLICATION

This application claims priority based on International Patent Application No. PCT/EP2005/052042, filed on May 4, 2005.

FIELD OF THE INVENTION

The present invention describes the preparation of low molecular weight hormone mimetics that selectively have agonistic activity on the FSH receptor.

BACKGROUND OF THE INVENTION

Gonadotropins serve important functions in a variety of bodily functions including metabolism, temperature regulation and the reproductive process. Gonadotropins act on specific gonadal cell types to initiate ovarian and testicular differentiation and steroidogenesis. The hypophyseal gonadotropin FSH (follicle stimulating hormone) for example plays a pivotal role in the stimulation of follicle development and maturation whereas LH (luteinizing hormone) induces ovulation (Sharp, R. M. Clin Endocrinol. 33:787-807, 1990; Dorrington and Armstrong, Recent Prog. Horm. Res. 35:301-342, 1979). Currently, FSH is applied clinically, in combination with LH, for ovarian stimulation i.e. ovarian hyperstimulation for in vitro fertilisation (IVF) and induction of ovulation in infertile anovulatory women (Insler, V., Int. J. Fertility 33:85-97, 1988, Navot and Rosenwaks, J. Vitro Fert. Embryo Transfer 5:3-13, 1988), as well as for male hypogonadism and male infertility.

The gonadotropin FSH is released from the anterior pituitary under the influence of gonadotropin-releasing hormone and oestrogens, and from the placenta during pregnancy. In the female, FSH acts on the ovaries promoting development of follicles and is the major hormone regulating secretion of oestrogens. In the male, FSH is responsible for the integrity of the seminiferous tubules and acts on Sertoli cells to support gametogenesis. Purified FSH is used clinically to treat infertility in females and for some types of failure of spermatogenesis in males. Gonadotropins destined for therapeutic purposes can be isolated from human urine sources and are of low purity (Morse et al, Amer. J. Reproduct. Immunol. and Microbiology 17:143, 1988). Alternatively, they can be prepared as recombinant gonadotropins. Recombinant human FSH is available commercially and is being used in assisted reproduction (Olijve et al. Mol. Hum. Reprod. 2:371, 1996; Devroey et al. Lancet 339:1170, 1992). The actions of the FSH hormone are mediated by a specific plasma membrane receptor that is a member of the large family of G-protein coupled receptors. These receptors consist of a single polypeptide with seven transmembrane domains and are able to interact with the Gs protein, leading to the activation of adenylate cyclase The FSH receptor is a highly specific target in the ovarian follicle growth process and is exclusively expressed in the ovary. Blocking of the receptor or inhibiting the signalling which is normally induced after FSH-mediated receptor activation will disturb follicle development and thus ovulation and fertility. Low molecular weight FSH antagonists could form the basis for new contraceptives, while low molecular weight FSH agonists can be used for the same clinical purposes as native FSH, i.e. for the treatment of infertility and for ovarian hyperstimulation on behalf of in vitro fertilisation.

Low molecular weight FSH mimetics with agonistic properties were disclosed in the International Application WO 2000/08015 (Applied Research Systems ARS Holding N.V.) and in WO 2002/09706 (Affymax Research Institute).

Certain tetrahydroquinoline derivatives have recently been disclosed in the International Application WO2003/004028 (AKZO NOBEL N.V.) as FSH modulating substances, either having agonistic or antagonistic properties.

DETAILED DESCRIPTION OF THE INVENTION

The present invention describes the preparation of low molecular weight hormone mimetics that selectively activate the FSH receptor.

Thus, it has now been found, that the following class of dihydropyridine compounds of formula I or pharmaceutically acceptable salts thereof, have FSH receptor agonistic activity:

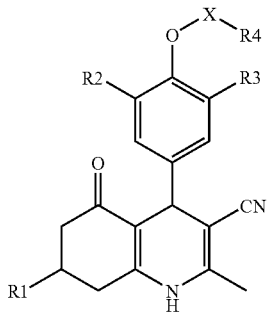

Formula I
wherein
$R^1$ is (1-6C)alkyl, (2-6C)alkenyl, (2-6C)alkynyl, phenyl or (1-5C)heteroaryl $R^2$, $R^3$ are independently (1-4C)alkyl, (2-4C)alkenyl, (2-4C)alkynyl, (1-4C)alkoxy, (2-4C)alkenyloxy, (3-4C)alkynyloxy, halogen X is $SO_2$, $CH_2$, C(O) or X is a bond $R^4$ is (1-6C)alkyl, (2-6C)alkenyl, (2-6C)alkynyl, (3-6C)cycloalkyl, (3-6C)cycloalkenyl, (3-6C)cycloalkyl(1-4C)alkyl, (2-6C)heterocycloalkyl, (2-6C)heterocycloalkyl(1-4C)alkyl, (6-10C)aryl, (6-10C)aryl(1-4C)alkyl, (1-9C)heteroaryl or (1-9C)heteroaryl(1-4C)alkyl.

If X is $CH_2$, $R^4$ may furthermore be $R^5$-oxycarbonyl or $R^5$-carbonyl.

If $R^4$ is phenyl, phenyl may, in addition to the substituents for (6-10C)aryl groups as mentioned in the definitions, optionally be substituted with one or more substituents from the following groups:
(1-4C)alkylthio, (1-4C)alkylsulfonyl, $R^5$-oxycarbonyl, $R^5$-carbonyl or $R^5,R^6$-aminocarbonyl.

$R^5$, $R^6$ independently is H, (1-4C)alkyl, (2-4C)alkenyl, (2-4C)alkynyl, (3-6C)cycloalkyl, (3-6C)cycloalkyl(1-4C)alkyl, (2-6C)heterocycloalkyl, (2-6C)heterocycloalkyl(1-4C)alkyl, (1-4C)alkoxycarbonyl(1-4C)alkyl, (1-4C)(di)alkylaminocarbonyl(1-4C)alkyl, (6-10C)aryl, (1-9C)heteroaryl, (6-10C)aryl(1-4C)alkyl, (1-9C)heteroaryl(1-4C)alkyl, (6-10C)arylaminocarbonyl(1-4C)alkyl, (1-9C)heteroarylaminocarbonyl(1-4C)alkyl or $R^5,R^6$ may be joined in a (2-6C)heterocycloalkyl ring.

The compounds according to the present invention modulate the FSH receptor function and can be used for the same clinical purposes as native FSH since they behave like agonists, with the advantage that they may display altered stability properties and may be administered differently.

Thus, the FSH-receptor agonists of the present invention may be used for treating infertility. Preferably the compounds of the present invention are used to activate the FSH-receptor.

The term (1-4C)alkyl as used in the definition means a branched or unbranched alkyl group having 1-4 carbon atoms, being methyl, ethyl, propyl, isopropyl, butyl, sec-butyl and tert-butyl.

The term (1-6C)alkyl means a branched or unbranched alkyl group having 1-6 carbon atoms, for example methyl, ethyl, propyl, isopropyl, butyl, tert-butyl, n-pentyl and n-hexyl. (1-5C)Alkyl groups are preferred, (1-4C)alkyl being the most preferred.

The term (2-6C)alkenyl means a branched or unbranched alkenyl group having 2-6 carbon atoms, such as ethenyl, 2-butenyl, and n-pentenyl.

The term (2-4C)alkenyl means a branched or unbranched alkenyl group having 2-4 carbon atoms, such as ethenyl, n-propenyl and 2-butenyl.

The term (2-6C)alkynyl means a branched or unbranched alkynyl group having 2-6 carbon atoms, such as ethynyl, propynyl and n-pentynyl.

The term (2-4C)alkynyl means an alkynyl group having 2-4 carbon atoms, such as ethynyl and propynyl.

The term (3-6C)cycloalkyl means a cycloalkyl group having 3-6 carbon atoms, being cyclopropyl, cyclobutyl, cyclopentyl and cyclohexyl.

The term (3-6C)cycloalkenyl means a cycloalkenyl group having 3-6 carbon atoms, such as cyclopropenyl, cyclopentenyl and cyclohexenyl.

The term (3-6C)cycloalkyl(1-4C)alkyl means a cycloalkylalkyl group, the cycloalkyl group of which has 3-6 carbon atoms with the same meaning as previously defined and the alkyl group having 1-4 carbon atoms with the same meaning as previously defined.

The term (2-6C)heterocycloalkyl means a heterocycloalkyl group having 2-6 carbon atoms, preferably 3-5 carbon atoms, and at least including one heteroatom selected from N, O and/or S, which may be attached via a heteroatom if feasible, or a carbon atom. Preferred heteroatoms are N or O. Most preferred are piperidinyl, morpholinyl, pyrrolidinyl and piperazinyl.

The term (2-6C)heterocycloalkyl(1-4C)alkyl means a heterocycloalkylalkyl group, the heterocycloalkyl group of which has 2-6 carbon atoms with the same meaning as previously defined and the alkyl group having 1-4 carbon atoms with the same meaning as previously defined.

The term (1-4C)alkoxy means an alkoxy group having 1-4 carbon atoms, the alkyl moiety having the same meaning as previously defined. (1-2C)Alkoxy groups are preferred.

The term (1-4C)alkylthio means an alkylthio group having 1-4 carbon atoms, the alkyl moiety having the same meaning as previously defined.

The term (2-4C)alkenyloxy means an alkenyloxy group having 2-4 carbon atoms, the alkenyl moiety having the same meaning as previously defined.

The term (3-4C)alkynyloxy means an alkynyloxy group having 3-4 carbon atoms, the alkynyl moiety having the same meaning as previously defined.

The term (6-10C)aryl means an aromatic hydrocarbon group having 6-10 carbon atoms, such as phenyl, naphthyl, tetrahydronaphthyl or indenyl, which may optionally be substituted with one or more substituents selected from hydroxy, amino, halogen, nitro, trifluoromethyl, cyano, (1-4C)alkyl, (2-4C)alkenyl, (2-4C)alkynyl, (1-4C)alkoxy, or (1-4C)(di) alkylamino, the alkyl moieties having the same meaning as previously defined. The preferred aromatic hydrocarbon group is phenyl.

The term (1-9C)heteroaryl means a substituted or unsubstituted aromatic group having 1-9 carbon atoms, at least including one heteroatom selected from N, O and/or S, like tetrazolyl, imidazolyl, thiadiazolyl, pyridinyl, (benzo)thienyl, (benzo)furyl, (iso)quinolinyl, tetrahydro(iso)quinolinyl, coumarinyl, quinoxalinyl or indolyl. The substituents on the (1-9C)heteroaryl group may be selected from the group of substituents listed for the (6-10C)aryl group. (1-5C)hetroaryl is preferred. The (1-9C)heteroaryl group may be attached via a carbon atom or a heteroatom, if feasible.

The term (1-5C)heteroaryl means a substituted or unsubstituted aromatic group having 1-5 carbon atoms, at least including one heteroatom selected from N, O and/or S, like tetrazolyl, imidazolyl, thiadiazolyl, pyridinyl, thienyl or furyl, furyl being the most preferred. Preferred heteroaryl groups are thienyl, furyl and pyridinyl. The substituents on the (1-5C)heteroaryl group may be selected from the group of substituents listed for the (6-10C)aryl group.

The term (6-10C)aryl(1-4C)alkyl means an arylalkyl group, the aryl group of which contains 6-10 carbon atoms with the same meaning as previously defined and the alkyl group contains 1-4 carbon atoms with the same meaning as previously defined. Most preferred is benzyl.

The term (1-9C)heteroaryl(1-4C)alkyl means a heteroarylalkyl group, the heteroaryl group of which contains 1-9 carbon atoms with the same meaning as previously defined and the alkyl group contains 1-4 carbon atoms with the same meaning as previously defined.

The term (1-4C)alkylsulfonyl means an alkylsulfonyl group, the alkyl group of which contains 1-4 carbon atoms with the same meaning as previously defined.

The term (1-4C)alkoxycarbonyl means an (1-4C)alkoxycarbonyl group, the alkoxy group of which contains 1-4 carbon atoms with the same meaning as previously defined. (1-2C)Alkoxycarbonyl groups are preferred The term (1-4C)alkoxycarbonyl(1-4C)alkyl means an alkoxycarbonylalkyl group, the alkyl groups of which contain 1-4 carbon atoms with the same meaning as previously defined.

The term (1-4C)(di)alkylaminocarbonyl(1-4C)alkyl means a (di)alkylaminocarbonylalkyl group, the alkyl groups of which contain 1-4 carbon atoms with the same meaning as previously defined.

The term halogen means fluorine, chlorine, bromine or iodine.

The term pharmaceutically acceptable salt represents those salts which are, within the scope of medical judgement, suitable for use in contact for the tissues of humans and lower animals without undue toxicity, irritation, allergic response and the like, and are commensurate with a reasonable benefit/risk ratio. Pharmaceutically acceptable salts are well known in the art. They may be obtained during the final isolation and purification of the compounds of the invention, or separately by reacting the free base function with a suitable mineral acid such as hydrochloric acid, phosphoric acid, or sulfuic acid, or with an organic acid such as for example ascorbic acid, citric acid, tartaric acid, lactic acid, maleic acid, malonic acid, fumaric acid, glycolic acid, succinic acid, propionic acid, acetic acid, methanesulfonic acid, and the like. The acid function can be reacted with an organic or a mineral base, like sodium hydroxide, potassium hydroxide or lithium hydroxide.

The invention also relates to compounds of formula I, wherein $R^1$ is (1-6C)alkyl, phenyl or (1-5C)heteroaryl, all optionally substituted with the substituents as mentioned in the definitions. More in particular, the invention relates to compounds wherein $R^1$ is (1-4C)alkyl, phenyl or 4C-heteroaryl. The invention also concerns compounds wherein $R^1$ is n-propyl or furyl.

Another aspect of the invention are compounds according to formula I wherein $R^2, R^3$ is halogen and/or (1-4C)alkoxy.

In yet another aspect, the invention concerns compounds of formula I, wherein X is $CH_2$.

Another aspect of the invention is a compound wherein $R^4$ is phenyl, optionally substituted with the substituents as mentioned in the definitions. In another aspect the invention relates to compounds wherein $R^4$ is phenyl which is substituted at the ortho and/or meta positions. In yet another aspect, the invention concerns compounds of formula I wherein $R^4$ is phenyl, substituted with $R^5, R^6$-aminocarbonyl, (1-4C)alkoxy and/or halogen. In yet another aspect, the invention relates to compounds wherein $R^5, R^6$-in $R^5, R^6$ aminocarbonyl is (1-4C)(di)alkylamino, (1-4C)alkoxycarbonyl(1-4C)alkyl. or (1-9C)heteroaryl(1-4C)alkyl. In yet another aspect, at least one of $R^5, R^6$-in $R^5, R^6$ aminocarbonyl is H.

In another aspect the invention concerns compounds wherein (6-10C)aryl, (6-10C)aryl(1-4C)alkyl, (1-9C)heteroaryl or (1-9C)heteroaryl(1-4C)alkyl in $R^4$ are not substituted.

Still another aspect of the invention concerns compounds wherein $X=CH_2$ and in which $R^4$ is phenyl, optionally substituted with the substituents as mentioned in the definitions.

Yet another aspect of the invention concerns compounds wherein all specific definitions of the groups $R^1$ through $R^4$ and X as defined here above are combined in the dihydropyridine compound of formula I.

Excluded from the invention is the compound 2-methyl-5-oxo-7-phenyl-4-(3,4,5-trimethoxyphenyl)-1,4,5,6,7,8-hexahydroquinoline-3-carbonitrile.

The disclaimer relates to CAS330674-72-1, available from commercial sources like Chembridge Corp, MicroChemistry Ltd, Ambinter, Asinex, Scientific Exchange Inc, and ChemDiv Inc.

Suitable methods for the preparation of the compounds of the invention are outlined below.

The 1,4-dihydropyridine derivatives I of the present invention can be prepared starting from cyclohexane-1,3-diones of general formula II, benzaldehydes of general formula III and 3-aminocrotonitrile IV, in which $R^1$, $R^2$, $R^3$, $R^4$ and X are as previously defined, by the well-documented three component Hantzsch-type cyclo-condensation reaction.

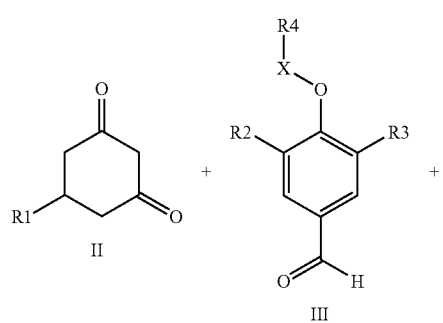

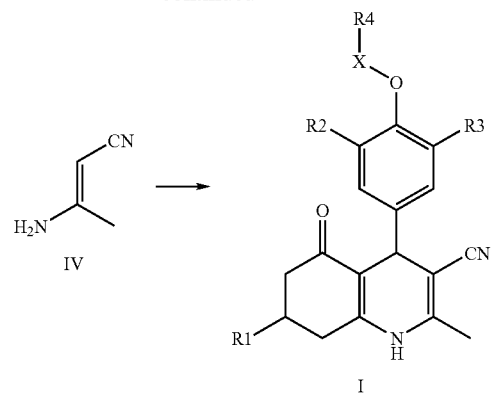

Related Hantzsch-type cyclo-condensation reactions can be found in: Bioorg. Med. Chem. Lett. 12 (2002) 1481-1484, J. Chem. Soc., Perkin Trans. 1 (2002) 1141-1156, Synlett (2002) 89-92, Drug Dev. Res. 51 (2000) 233-243, J. Med. Chem. 42 (1999) 1422-1427, ibid. 5266-5271, ibid. 41 (1998) 2643-2650, WO 9408966, Arzneim.-Forsch./Drug Res. 45 (1995) 1054-1056, J. Med. Chem. 34 (1991) 2248-2260, ibid. 17 (1974) 956-65, Chem. Rev. 72 (1972), 142. The above mentioned reaction is typically conducted at elevated temperature in a protic solvent like for example acetic acid, (iso)propanol, ethanol, methanol or mixtures thereof.

Alternatively, compounds of general formula I can be synthesized by first reacting the cyclohexane-1,3-diones of formula II with benzaldehydes of formula III in the presence of a base such as, but not limited to, ammonium acetate and then reacting the intermediate 2-benzylidene-cyclohexane-1,3-dione of general formula V, in which $R^1$, $R^2$, $R^3$, $R^4$ and X have the same meaning as previously defined, with 3-aminocrotonitrile IV.

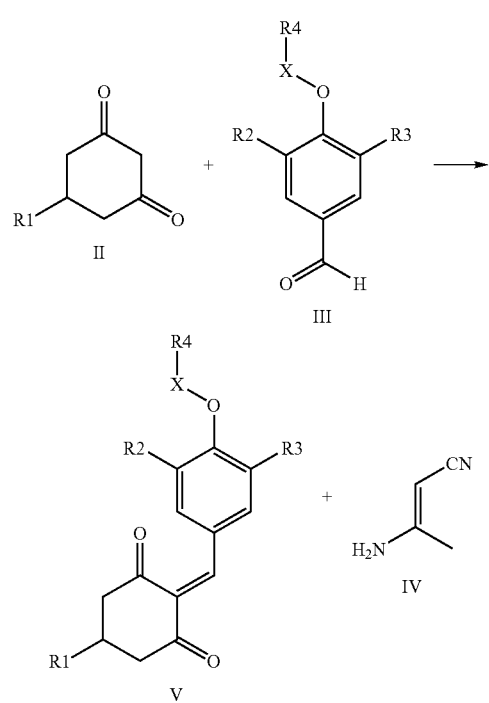

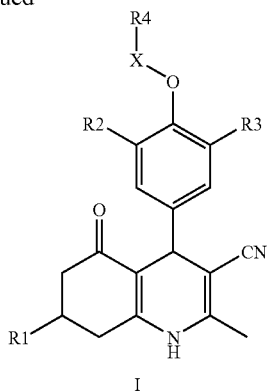

I

Compounds of general formula I-a wherein X=bond and R⁴=H, can be used to prepare compounds I-b-e by O-alkylation, O-(hetero)arylation, O-acylation or O-sulfonylation using standard conditions, well known to those skilled in the art.

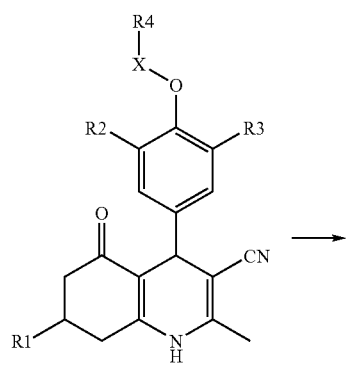

I-a: X = bond, R⁴ = H

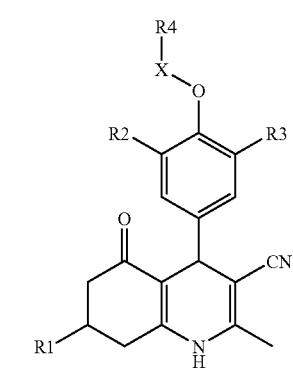

I-b: X = CH₂, R⁴ = as previously defined
I-c: X = bond, R⁴ = as previously defined
I-d: X = C(O), R⁴ = as previously defined
I-e: X = SO₂, R⁴ = as previously defined In a typical experiment, compounds I-a are reacted in a solvent, such as dichloromethane, N,N-dimethylformamide, dimethyl sulfoxide, ethanol, tetrahydrofuran, dioxane, toluene, 1-methyl-pyrrolidin-2-one or pyridine with an alkyl halide or acyl halide or acid anhydride or sulfonyl halide, or (hetero)aryl halide in the presence of a base such as, but not limited to, triethylamine, N,N-diisopropylethylamine (DiPEA), potassium carbonate, cesium carbonate or sodium hydride, optionally in the presence of a catalytic amount of potassium iodide or tetrabutylammonium iodide, and/or a Cu- or Pd-catalyst, to give O-alkylated, O-(hetero)arylated, O-acylated or O-sulfonylated derivatives of formula I-b, I-c, I-d, and I-e, respectively.

Compounds of formula I-f wherein X=CH₂ and R⁴=alkyl acid derivative or (hetero)aryl acid derivative, obtained by base-mediated (e.g. NaOH) saponification of a corresponding alkyl ester, can be condensed with amines of general structure R⁵,R⁶NH or alcohols of general structure R⁵OH using a coupling reagent such as diisopropyl carbodiimide (DIC), (3-dimethylaminopropyl)-ethyl-carbodiimide (EDCI), O-(benzotriazol-1-yl)-N,N,N',N'-tetramethyluronium hexafluorophosphate (TBTU) or O-(7-azabenzotriazol-1-yl)-N,N,N',N'-tetramethyluronium hexafluorophosphate (HATU) and a tertiary amine base (e.g. DIPEA) in a solvent such as ANN-dimethylformamide or dichloromethane at ambient or elevated temperature to give compounds of formula I-g and I-h.

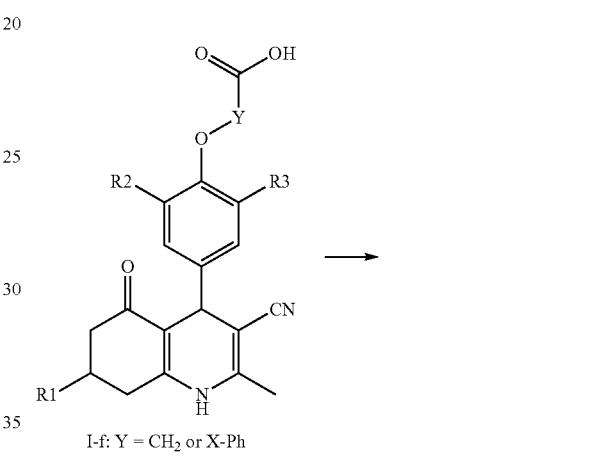

I-f: Y = CH₂ or X-Ph

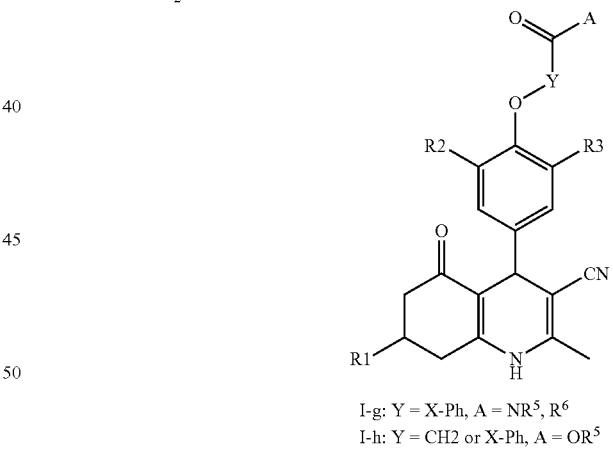

I-g: Y = X-Ph, A = NR⁵, R⁶
I-h: Y = CH2 or X-Ph, A = OR⁵

The substituted cyclohexane-1,3-diones of general formula II are commercially available or can be prepared by literature procedures known in the art. Relevant examples are found in: J. Med. Chem. 43 (2000) 4678-4693, Tetrahedron 56 (2000) 4753-4758, J. Med. Chem. 35 (1992) 3429-3447, ibid. 24 (1981) 1026-1034, Org. Synt. Coll. Vol. V (1973) 400, Chem. Ber. 88 (1955) 316-327, Justus Liebig Ann. Chem. 570 (1950) 15-31.

Benzaldehydes of general formula III also are commercially available or can be prepared according to literature procedures: J. Chem. Soc., Perkin Trans. 2 (2000) 1119-1124, J. Chem. Soc., Chem. Commun. 4 (1993) 419-420, Synth. Commun. 20 (1990) 2659-2666, Chem. Pharm. Bull. 34

(1986) 121-129, Indian J. Chem. Sect. B 20 (1981) 1010-1013, Monatsh. Chem. 106 (1975) 1191-1201, DE 1070162, J. Org. Chem. 23 (1958) 120.

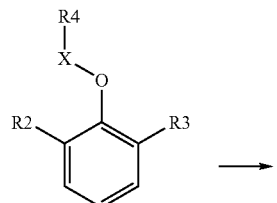

III-a: X = bond, $R^4$ = H

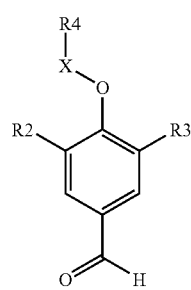

III-b: X = $CH_2$, $R^4$ = as previously defined
III-c: X = bond, $R^4$ = as previously defined
III-d: X = C(O), $R^4$ = as previously defined
III-e: X = $SO_2$, $R^4$ = as previously defined Alternatively, compounds III-a wherein X=bond and $R^4$=H can be used to synthesize compounds III-b-e by O-alkylation, O-arylation, O-acylation or O-sulfonylation using the same standard conditions as described above for compounds I-a.

The compounds of the present invention possess at least two chiral carbon atoms and may therefore be obtained as pure enantiomers, or as a mixture of enantiomers, or as a mixture of diastereomers. Methods for obtaining the pure enantiomers are well known in the art, e.g crystallization of salts which are obtained from optically active acids and the racemic mixture, or chromatography using chiral columns. For separation of diastereomers, straight phase or reversed phase columns may be used.

The compounds of the invention may form hydrates or solvates. It is known to those of skill in the art that charged compounds form hydrated species when lyophilized with water, or form solvated species when concentrated in a solution with an appropriate organic solvent. The compounds of this invention include the hydrates or solvates of the compounds listed.

For selecting active compounds testing at $10^{-5}$ M must result in an activity of more than 20% of the maximal activity when FSH is used as a reference. Another criterion might be the $EC_{50}$ value which must be $<10^{-5}$ M, preferably $<10^{-7}$ M, even more preferably $<10^{-9}$ M.

The skilled artisan will recognize that desirable $EC_{50}$ values are dependent on the compound tested. For example, a compound with an $EC_{50}$ which is less than $10^{-5}$ M is generally considered a candidate for drug selection. Preferably this value is lower than $10^{-7}$ M. However, a compound which has a higher $EC_{50}$, but is selective for the particular receptor, may be even a better candidate.

Methods to determine receptor binding, as well as in vitro and in vivo assays to determine biological activity, of gonadotropins are well known. In general, expressed receptor is contacted with the compound to be tested and binding or stimulation or inhibition of a functional response is measured.

To measure a functional response, isolated DNA encoding the FSH receptor gene, preferably the human receptor, is expressed in suitable host cells. Such a cell might be the Chinese Hamster Ovary cell, but other cells are also suitable. Preferably the cells are of mammalian origin (Jia et al, Mol. Endocrin., 5:759-776, 1991).

Methods to construct recombinant FSH expressing cell lines are well known in the art (Sambrook et al., Molecular Cloning: a Laboratory Manual, Cold Spring Harbor Laboratory Press, Cold Spring Harbor, latest edition). Expression of receptor is attained by expression of the DNA encoding the desired protein. Techniques for site directed mutagenesis, ligation of additional sequences, PCR, and construction of suitable expression systems are all, by now, well known in the art. Portions, or all, of the DNA encoding the desired protein can be constructed synthetically using standard solid phase techniques, preferably to include restriction sites for ease of ligation. Suitable control elements for transcription and translation of the included coding sequence can be provided to the DNA coding sequences. As is well known, expression systems are now available which are compatible with a wide variety of hosts, including prokaryotic hosts such as bacteria and eukaryotic hosts such as yeast, plant cells, insect cells, mammalian cells, avian cells and the like.

Cells expressing the receptor are then contacted with the test compound to observe binding, or stimulation or inhibition of a functional response.

Alternatively, isolated cell membranes containing the expressed receptor may be used to measure binding of compound.

For measurement of binding, radioactive or fluorescent compounds may be used. As reference compound human recombinant FSH can be used.

In the alternative also competition binding assays may be performed

Another assay involves screening for FSH receptor agonist compounds by determining stimulation of receptor mediated cAMP accumulation. Thus, such a method involves expression of the receptor on the cell surface of a host cell and exposing the cell to the test compound. The amount of cAMP is then measured. The level of cAMP will be increased, by the stimulating effect of the test compound upon binding to the receptor.

In addition to direct measurement of e.g. cAMP levels in the exposed cell, cells lines can be used which in addition to transfection with receptor encoding DNA are also transfected with a second DNA encoding a reporter gene the expression of which responds to the level of cAMP. Such reporter genes might be cAMP inducible or might be constructed in such a way that they are connected to novel cAMP responsive elements. In general, reporter gene expression might be controlled by any response element reacting to changing levels of cAMP. Suitable reporter genes are e.g. LacZ, alkaline phosphatase, firefly luciferase and green fluorescence protein. The principles of such transactivation assays are well known in the art and are described e.g. in Stratowa, Ch., Himmler, A. and Czernilofsky, A. P., (1995) Curr. Opin. Biotechnol. 6:574.

The present invention also relates to a pharmaceutical composition comprising a dihydropyridine derivative or pharmaceutically acceptable salts thereof having the general formula I in admixture with pharmaceutically acceptable auxiliaries and optionally other therapeutic agents. The auxiliaries must be "acceptable" in the sense of being compatible with the other ingredients of the composition and not deleterious to the recipients thereof. The pharmaceutical compositions may also comprise 2-methyl-5-oxo-7-phenyl-4-(3,4,5-trimethoxyphenyl)-1,4,5,6,7,8-hexahydroquinoline-3-carbonitrile.

Compositions include e.g. those suitable for oral, sublingual, subcutaneous, intravenous, intramuscular, nasal, local, or rectal administration, and the like, all in unit dosage forms for administration.

For oral administration, the active ingredient may be presented as discrete units, such as tablets, capsules, powders, granulates, solutions, suspensions, and the like.

For parenteral administration, the pharmaceutical composition of the invention may be presented in unit-dose or multi-dose containers, e.g. injection liquids in predetermined amounts, for example in sealed vials and ampoules, and may also be stored in a freeze dried (lyophilized) condition requiring only the addition of sterile liquid carrier, e.g. water, prior to use.

Mixed with such pharmaceutically acceptable auxiliaries, e.g. as described in the standard reference, Gennaro, A. R. et al., Remington: *The Science and Practice of Pharmacy* (20th Edition., Lippincott Williams & Wilkins, 2000, see especially Part 5: Pharmaceutical Manufacturing), the active agent may be compressed into solid dosage units, such as pills, tablets, or be processed into capsules or suppositories. By means of pharmaceutically acceptable liquids the active agent can be applied as a fluid composition, e.g. as an injection preparation, in the form of a solution, suspension, emulsion, or as a spray, e.g. a nasal spray.

For making solid dosage units, the use of conventional additives such as fillers, colorants, polymeric binders and the like is contemplated. In general any pharmaceutically acceptable additive which does not interfere with the function of the active compounds can be used. Suitable carriers with which the active agent of the invention can be administered as solid compositions include lactose, starch, cellulose derivatives and the like, or mixtures thereof, used in suitable amounts. For parenteral administration, aqueous suspensions, isotonic saline solutions and sterile injectable solutions may be used, containing pharmaceutically acceptable dispersing agents and/or wetting agents, such as propylene glycol or butylene glycol.

The invention further includes a pharmaceutical composition, as hereinbefore described, in combination with packaging material suitable for said composition, said packaging material including instructions for the use of the composition for the use as hereinbefore described.

The exact dose and regimen of administration of the active ingredient, or a pharmaceutical composition thereof, may vary with the particular compound, the route of administration, and the age and condition of the individual subject to whom the medicament is to be administered.

In general parenteral administration requires lower dosages than other methods of administration which are more dependent upon absorption. However, a suitable dosage for humans may be 0.05-25 mg per kg body weight. The desired dose may be presented as one dose or as multiple subdoses administered at appropriate intervals throughout the day, or, in case of female recipients, as doses to be administered at appropriate daily intervals throughout the menstrual cycle. The dosage as well as the regimen of administration may differ between a female and a male recipient.

Thus, the compounds according to the invention can be used in therapy.

A further aspect of the invention resides in the use of a dihydropyridine derivative compound having the general formula I for the manufacture of a medicament to be used for the treatment of disorders responsive to FSH receptor mediated pathways, preferably for the treatment of infertility.

The invention is illustrated by the following examples.

EXAMPLES

Example 1

4-(3-Bromo-4-ethoxy-5-methoxyphenyl)-2-methyl-5-oxo-7-phenyl-1,4,5,6,7,8-hexahydroquinoline-3-carbonitrile a) 4-(3-Bromo-4-hydroxy-5-methoxyphenyl-2-methyl-5-oxo-7-phenyl-1,4,5,6,7,8-hexahydroquinoline-3-carbonitrile A mixture of 5-phenylcyclohexane-1,3-dione (0.51 g), 3-bromo-5-methoxy-4-hydroxybenzaldehyde (0.62 g) and 3-aminocrotonitrile (0.22 g) in 20 mL absolute ethanol was stirred at 75° C. for 3 h. The reaction mixture was concentrated and the title compound was obtained as a off-white solid after flash column chromatography (silica gel, heptane/ethyl acetate (3/7, v/v), $R_f$=0.36).

Yield: 0.95 g. MS-ESI: [M−H]$^-$=463/465.

b) 4-(3-Bromo-4-ethoxy-5-methoxyphenyl)-2-methyl-5-oxo-7-phenyl-1,4,5,6,7,8-hexahydroquinoline-3-carbonitrile A mixture of the product of step a (15 mg), ethyl iodide (6.4 μL), sodium hydride (2.6 mg, 60% in oil) and tetrabutylammonium iodide (1.2 mg) in 0.5 mL of NMP was stirred at 80° C. for 2 h. Water was added and the reaction mixture was extracted with ethyl acetate. The organic phases were concentrated and the title compound was obtained after flash column chromatography (silica gel, heptane/ethyl acetate (1/4, v/v), $R_f$=0.52).

Yield: 2.2 mg. MS-ESI: [M−H]$^-$=491/493.

Example 2

4-(3-Bromo-4-cyclohexylmethoxy-5-methoxyphenyl-2-methyl-5-oxo-7-phenyl-1,4,5,6,7,8-hexahydroquinoline-3-carbonitrile The title compound was obtained analogously to example 1b, starting from the product of example 1a (15 mg) and bromomethylcyclohexane (12 μL).

Yield: 12 mg. $R_f$ (heptane/ethyl acetate (1/4, v/v))=0.59. MS-ESI: [M−H]$^-$=559/561.

Example 3

4-[3-Bromo-5-methoxy-4-(3-methylbutoxy)-phenyl]-2-methyl-5-oxo-7-phenyl-1,4,5,6,7,8-hexahydroquinoline-3-carbonitrile The title compound was obtained analogously to example 1b, starting from the product of example 1a (15 mg) and 1-iodo-3-methylbutane (4.7 μL).

Yield: 14 mg. $R_f$ (heptane/ethyl acetate (1/4, v/v))=0.56. MS-ESI: [M−H]⁻=533/535.

Example 4

4-[3-Bromo-4-(5-chlorothiophen-2-ylmethoxy)-5-methoxyphenyl]-2-methyl-5-oxo-7-phenyl-1,4,5,6,7,8-hexahydroquinoline-3-carbonitrile A mixture of the product of example 1a (15 mg), 2-chloro-5-chloromethylthiophene (4.3 µL) and cesium carbonate (21 mg) in 1 mL of dioxane was stirred at 80° C. for 4 h. The reaction mixture was concentrated and the title compound was obtained after flash column chromatography (silica gel, heptane/ethyl acetate (3/7, v/v), $R_f$=0.38).

Yield: 4.7 mg. MS-ESI: [M−H]⁻=593/595/597.

Example 5

[2-Bromo-4-(3-cyano-2-methyl-5-oxo-7-phenyl-1,4,5,6,7,8-hexahydroquinolin-4-yl)-6-methoxyphenoxy]-acetic acid methyl ester The title compound was obtained analogously to example 4, starting from the product of example 1a (0.47 g) and bromoacetic acid methyl ester (1.0 mL).

Yield: 0.32 g. $R_f$ (heptane/ethyl acetate (1/4, v/v))=0.46. MS-ESI: [M−H]⁻=535/537.

Example 6

3-Methoxybenzoic acid 2-bromo-4-(3-cyano-2-methyl-5-oxo-7-phenyl-1,4,5,6,7,8-hexahydroquinolin-4-yl)-6-methoxyphenyl ester The title compound was obtained analogously to example 4, starting from the product of example 1a (15 mg) and 3-methoxy-benzoyl chloride (5.4 µL).

Yield: 7.4 mg. $R_f$ (heptane/ethyl acetate (1/4, v/v))=0.48. MS-ESI: [M−H]⁻=597/599.

Example 7

4-[3-Bromo-4-(3-cyanobenzyloxy-5-methoxyphenyl]-2-methyl-5-oxo-7-phenyl-1,4,5,6,7,8-hexahydroquinoline-3-carbonitrile The title compound was obtained analogously to example 4, starting from the product of example 1a (15 mg) and 3-bromomethylbenzonitrile (7.6 mg).

Yield: 15 mg. $R_f$ (heptane/ethyl acetate (1/4, v/v))=0.51. MS-ESI: [M−H]⁻=578/580.

Example 8

4-[3-Bromo-5-methoxy-4-(naphthalen-2-ylmethoxyphenyl]-2-methyl-5-oxo-7-phenyl-1,4,5,6,7,8-hexahydroquinoline-3-carbonitrile The title compound was obtained analogously to example 4, starting from the product of example 1a (15 mg) and 2-bromomethylnaphthalene (8.6 mg).

Yield: 11 mg. $R_f$ (heptane/ethyl acetate (1/4, v/v))=0.60. MS-ESI: [M−H]⁻=603/605.

Example 9

Phenylmethanesulfonic acid 2-bromo-4-(3-cyano-2-methyl-5-oxo-7-phenyl-1,4,5,6,7,8-hexahydroquinolin-4-yl)-6-methoxyphenyl ester A mixture of the product of example 1a (15 mg), phenyl-methanesulfonyl chloride (9.2 mg) and triethylamine (9.4 µL) in 1 mL of dichloromethane was stirred at room temperature for 2 h. The reaction mixture was concentrated and the title compound was obtained after flash column chromatography (silica gel, heptane/ethyl acetate (1/4, v/v), $R_f$=0.41).

Yield: 15 mg. MS-ESI: [M+H]⁺=619/621.

Example 10

Thiophene-2-sulfonic acid 2-bromo-4-(3-cyano-2-methyl-5-oxo-7-phenyl-1,4,5,6,7,8-hexahydroquinolin-4-yl)-6-methoxyphenyl ester The title compound was obtained analogously to example 9, starting from the product of example 1a (15 mg) and thiophene-2-sulfonyl chloride (8.8 mg).

Yield: 20 mg. $R_f$ (heptane/ethyl acetate (1/4, v/v))=0.30. MS-ESI: [M−H]⁻=611/613.

Example 11

4-[3,5-Dibromo-4-(3-methoxybenzyloxy)-phenyl]-7-ethyl-2-methyl-5-oxo-1,4,5,6,7,8-hexahydroquinoline-3-carbonitrile a) 3,5-dibromo-4-(3-methoxybenzyloxy)-benzaldehyde A mixture of 3,5-dibromo-4-hydroxybenzaldehyde (0.28 g), 1-bromomethyl-3-methoxybenzene (0.15 mL), potassium carbonate (0.29 g) and potassium iodide (42 mg) in 10 mL absolute ethanol was stirred at 80° C. for 2 days. The reaction mixture was concentrated and the title compound was obtained as a off-white solid after flash column chromatography (silica gel, heptane/ethyl acetate (3/7, v/v)), $R_f$=0.51).

Yield: 0.24 g. MS-ESI: [M−H]⁻=463/465. ¹H NMR (CDCl₃): δ=9.88 (s, 1H), 8.06 (s, 1H), 7.34 (t, 1H), 7.18 (bs, 1H), 7.15 (d, 1H), 6.93 (dd, 1H), 5.10 (s, 2H), 3.85 (s, 3H).

b) 4-[3,5-Dibromo-4-(3-methoxybenzyloxy)-phenyl]-7-ethyl-2-methyl-5-oxo-1,4,5,6,7,8-hexahydroquinoline-3-carbonitrile The title compound was obtained analogously to example 1a, starting from 5-ethylcyclohexane-1,3-dione (8.5 mg) and the product of step a (24 mg).

Yield: 26 mg. $R_f$ (heptane/ethyl acetate (3/7, v/v))=0.40. MS-ESI: [M+H]⁺=585/587/589.

Example 12

4-{3-Bromo-5-ethoxy-4-[2-(3-nitrophenyl)-2-oxoethoxy]-phenyl}-2-methyl-5-oxo-7-phenyl-1,4,5,6,7,8-hexahydroquinoline-3-carbonitrile a) 4-(3-Bromo-5-ethoxy 4-hydroxyphenyl)-2-methyl-5-oxo-7-phenyl-1,4,5,6,7,8-hexahydroquinoline-3-carbonitrile The title compound was obtained analogously to example 1a, starting from 3-bromo-5-ethoxy-4-hydroxybenzaldehyde (0.15 g).

Yield: 0.15 g. $R_f$ (heptane/ethyl acetate (4/6, v/v))=0.18. MS-ESI: [M+H]$^+$=479/481.

b) 4-{3-Bromo-5-ethoxy-4-[2-(3-nitrophenyl)-2-oxoethoxy]-phenyl}-2-methyl-5-oxo-7-phenyl-1,4,5,6,7,8-hexahydroquinoline-3-carbonitrile The title compound was obtained analogously to example 4, starting from the product of step a (15 mg) and 2-bromo-1-(3-nitrophenyl)-ethanone (8.4 mg).
Yield: 14 mg. $R_f$ (heptane/ethyl acetate (1/4, v/v))=0.58. MS-ESI: [+H]$^+$=642/644.

Example 13

3-[2-Bromo-4-(3-cyano-2-methyl-5-oxo-7-phenyl-1,4,5,6,7,8-hexahydroquiolin-4-yl)-6-methoxyphenoxymethyl]-N-thiophen-2-ylmethylbenzamide a) 3-[2-Bromo-4-(3-cyano-2-methyl-5-oxo-7-phenyl-1,4,5,6,7,8-hexahydroquinolin-4-yl)-6-methoxyphenoxymethyl]-benzoic acid methyl ester The title compound was obtained analogously to example 4, starting from the product of example 1a (0.35 g) and 3-bromomethylbenzoic acid methyl ester (0.18 g).
Yield: 0.35 g. $R_f$ (heptane/ethyl acetate (3/7, v/v))=0.34. MS-ESI: [M+H]$^+$=613/615.

b) 3-[2-Bromo-4-(3-cyano-2-methyl-5-oxo-7-phenyl-1,4,5,6,7,8-hexahydroquinolin-4-yl)-6-methoxyphenoxymethyl]-benzoic acid A solution of the product of step a (0.35 g) was dissolved in 20 mL of dioxane/water (7/3, v/v) and 2 mL of 2 M NaOH in water was added. The reaction mixture was stirred for 5 days at room temperature. The reaction mixture was poured into water and acidified with 2 M HCl in water to pH 2 and was extracted several times with ethyl acetate. The organic phases were washed with water and saturated brine, dried over Na$_2$SO$_4$ and evaporated to give the title compound.
Yield: 0.35 g. MS-ESI: [M+H]$^+$=599/601.

c) 3-[2-Bromo-4-(3-cyano-2-methyl-5-oxo-7-phenyl-1,4,5,6,7,8-hexahydroquinolin-4-yl)-6-methoxyphenoxymethyl]-N-thiophen-2-ylmethylbenzamide To a solution of the product of step b (20 mg) in 2 mL of dichloromethane were added EDCI (7.0 mg), DIPEA (7 µL) and 2-thiophenemethylamine (4.1 µL) and the reaction mixture was stirred for 3 h. at room temperature. The reaction mixture was concentrated and the title compound was obtained after flash column chromatography (silica gel, heptane/ethyl acetate (1/4, v/v), $R_f$=0.78).
Yield: 11 mg. MS-ESI: [M+H]$^+$=694/696.

Example 14

3-[2-Bromo-4-(3-cyano-2-methyl-5-oxo-7-phenyl-1,4,5,6,7,8-hexahydroquinolin-4-yl)-6-methoxyphenoxymethyl]-benzoic acid 2-morpholin-4-ylethyl ester To a solution of the product of example 13b (20 mg) in 2 mL of dichloromethane were added TBTU (12 mg), DIPEA (7 µL) and 2-morpholin-4-ylethanol (4.8 µL) and the reaction mixture was stirred for 3 h. at room temperature. The reaction mixture was concentrated and the title compound was obtained after flash column chromatography (silica gel, heptane/ethyl acetate (1/4, v/v), $R_f$=0.48).
Yield: 11 mg. MS-ESI: [M+H]$^+$=694/696.

Example 15

4-{3-Bromo-5-ethoxy-4-[3-(piperidine-1-carbonyl)-benzyloxy]-phenyl}-2-methyl-5-oxo-7-phenyl-1,4,5,6,7,8-hexahydroquinoline-3-carbonitrile a) 3-(2-Bromo-6-ethoxy-4-formylphenoxymethyl)-benzoic acid methyl ester

3-Bromomethylbenzoic acid methyl ester (0.77 g), K$_2$CO$_3$ (1.0 g) and a catalytic amount of n-Bu$_4$NI were added to a solution of 5-bromo-3-ethoxy-4-hydroxybenzaldehyde (0.75 g) in 10 mL DMF and the reaction mixture was stirred at 70° C. for 1 h. A solution of 3% citric acid in water was added and the reaction mixture was extracted with ethyl acetate. The organic phases were washed with water and brine, dried over MgSO$_4$ and concentrated. The title compound was obtained after flash column chromatography (silica gel, heptane/ethyl acetate (1/4, v/v), $R_f$=0.25).
Yield: 1.08 g. $^1$H NMR (CDCl$_3$): δ=9.84 (s, 1H), 8.20 (bs, 1H), 8.02 (bd, 1H), 7.77 (d, 1H), 7.65 (d, 1H), 7.47 (t, 1H), 7.39 (d, 1H), 5.21 (s, 2H), 4.17 (q, 2H), 3.94 (s, 3H), 1.51 (t, 3H).

b) 3-[2-Bromo-4-(3-cyano-2-methyl-5-oxo-7-phenyl-1,4,5,6,7,8-hexahydroquinolin-4-yl)-6-ethoxyphenoxymethyl]-benzoic acid methyl ester The title compound was obtained analogously to example 1a, starting from the product of step a (0.26 g).
Yield: 0.27 g. $R_f$ (heptane/ethyl acetate (3/7, v/v))=0.34. MS-ESI: [M+H]$^+$=613/615.

c) 3-[2-Bromo-4-(3-cyano-2-methyl-5-oxo-7-phenyl-1,4,5,6,7,8-hexahydroquinolin-4-yl)-6-ethoxyphenoxymethyl]-benzoic acid The title compound was obtained analogously to example 13b, starting from the product of step b (0.27 g).
Yield: 0.27 g. MS-ESI: [M+H]$^+$=599/601.

d) 4-{3-Bromo-5-ethoxy-4-[3-(piperidine-1-carbonyl)-benzyloxy]-phenyl}-2-methyl-5-oxo-7-phenyl-1,4,5,6,7,8-hexahydroquinoline-3-carbonitrile The title compound was obtained analogously to example 13c, starting the product of step c (20 mg) and piperidine (3.9 µL).
Yield: 15 mg. $R_f$ (heptane/ethyl acetate (1/4, v/v))=0.25. MS-ESI: [M+H]$^+$=680/682.

Example 16

Glycine, N-3-[2-bromo-4-(3-cyano-2-methyl-5-oxo-7-phenyl-1,4,5,6,7,8-hexahydroquinolin-4-yl)-6-ethoxyphenoxymethyl]benzoyl methyl ester The title compound was obtained analogously to example 13c, starting from the product of example 15c (20 mg) and glycine methyl ester hydrochloride (4.9 mg).

Yield: 9.9 mg. $R_f$ (heptane/ethyl acetate (3/7, v/v))=0.16. MS-ESI: $[M+H]^+$=684/686.

Example 17

3-[2-Bromo-4-(3-cyano-7-ethyl-2-methyl-5-oxo-1,4,5,6,7,8-hexahydroquinolin-4-yl)-6-ethoxyphenoxymethyl]-benzoic acid methyl ester The title compound was obtained analogously to example 1a, starting from 5-ethylcyclohexane-1,3-dione (0.25 g) and the product of 15a (0.64 g).

Yield: 0.45 g. $R_f$ (heptane/ethyl acetate (1/4, v/v))=0.25. MS-ESI: $[M+H]^+$=579/581.

Example 18

3-[2-Bromo-4-(3-cyano-7-ethyl-2-methyl-5-oxo-1,4,5,6,7,8-hexahydro-quinolin-4-yl)-6-ethoxyphenoxymethyl]-benzoic acid The title compound was obtained analogously to example 13b, starting from the product of example 17 (0.43 g).

Yield: 0.38 g. $R_f$ (heptane/ethyl acetate (1/4, v/v))=0.17. MS-ESI: $[M+H]^+$=563/565.

Example 19

3-[2-Bromo-4-(3-cyano-7-ethyl-2-methyl-5-oxo-1,4,5,6,7,8-hexahydroquinolin-4-yl)-6-ethoxyphenoxymethyl]-N-tert-butylbenzamide To a solution of the product of example 18 (0.35 g) in 10 mL of dichloromethane were added tert-butylamine (0.12 mL), DIPEA (0.39 mL) and HATU (0.30 g) and the reaction mixture was stirred at 35° C. for 3 h. A solution of 3% citric acid in water was added and the obtained mixture was extracted several times with ethyl acetate. The organic phases were washed with water and brine, dried over $MgSO_4$ and concentrated. The title compound was obtained after flash column chromatography (silica gel, heptane/ethyl acetate (1/4, v/v), $R_f$=0.34).

Yield: 0.28 g. MS-ESI: $[M+H]^+$=620/622.

Example 20

3-[2-Bromo-4-(3-cyano-7-ethyl-2-methyl-5-oxo-1,4,5,6,7,8-hexahydroquinolin-4-yl)-6-ethoxyphenoxymethyl]-N-cyclohexylbenzamide The title compound was prepared analogously to example 13c, starting from the product of example 18 (20 mg) and cyclohexylamine (4.9 μL).

Yield: 7.9 mg. $R_f$ (silica gel, heptane/ethyl acetate (1/4, v/v)) 0.43. MS-ESI: $[M+H]^+$=646/648.

Example 21

3-[2-Bromo-4-(3-cyano-7-ethyl-2-methyl-5-oxo-1,4,5,6,7,8-hexahydroquinolin-4-yl)-6-ethoxyphenoxymethyl]-N-(2-morpholin-4-yl-ethyl)-benzamide The title compound was prepared analogously to example 13c, starting from the product of example 18 (20 mg) and 4-(2-aminoethyl)-morpholine (5.5 μL).

Yield: 15 mg. $R_f$ (dichloromethane/methanol (95/5, v/v))= 0.22. MS-ESI: $[M+H]^+$=677/679.

Example 22

4-[3-iodo-5-methoxy-4-(3-methoxybenzyloxy)-phenyl]-2-methyl-5-oxo-7-phenyl-1,4,5,6,7,8-hexahydroquinoline-3-carbonitrile a) 3-Iodo-5-methoxy-4-(3-methoxybenzyloxy)-benzaldehyde The title compound was obtained analogously to example 15a, starting from 4-hydroxy-3-iodo-5-methoxybenzaldehyde (0.70 g) and 1-bromomethyl-3-methoxybenzene (0.39 mL).

Yield: 0.56 g. $R_f$ (heptane/ethyl acetate (4/6, v/v))=0.42. $^1H$ NMR ($CDCl_3$): δ=9.83 (s, 1H), 7.86 (d, 1H), 7.43 (d, 1H), 7.29 (t, 1H), 7.16 (bs, 1H), 7.09 (d, 1H), 6.88 (dd, 1H), 5.14 (s, 2H), 3.95 (s, 3H), 3.84 (s, 3H).

b) 4-[3-iodo-5-methoxy-4-(3-methoxybenzyloxy)-phenyl]-2-methyl-5-oxo-7-phenyl-1,4,5,6,7,8-hexahydroquinoline-3-carbonitrile The title compound was prepared analogously to example 1a, starting from the product of step a (24 mg).

Yield: 17 mg. $R_f$ (heptane/ethyl acetate (1/4, v/v))=0.59. MS-ESI: $[M-H]^-$=631.

Example 23

4-[3-Bromo-4-(2-chloro-3-methoxybenzyloxy)-5-ethoxyphenyl]-2-methyl-5-oxo-7-propyl-1,4,5,6,7,8-hexahydroquinoline-3-carbonitrile The starting material was obtained according to the method described by McCarthy et al. (J. Org. Chem. 1986 (29) 1586):

a) 2-Chloro-3-methoxybenzaldehyde

At 40° C. n-butyl lithium (6.25 mL, 1.6 M in hexane) was added to a solution of N,N,N'-trimethylethylenediamine (1.27 mL) in 10 mL tetrahydrofuran. After 15 min. the reaction mixture was cooled to −70° C. and a solution of 3-methoxybenzaldehyde (1.22 mL) in 5 mL of tetrahydrofuran was added. The reaction mixture was allowed to warm to 0° C. and was cooled again to −70° C. and n-butyl lithium (6.25 mL, 1.6 M in hexane) was added. The reaction mixture was allowed to warm to 10° C. and was cooled again to −30° C. before it was added to a solution of hexachloroethane (7.10 g) in 10 mL tetrahydrofuran. The reaction mixture was stirred for 2 h. at room temperature, poured into 20 mL 10% HCl in water and extracted several times with ethyl acetate. The combined organic phases were washed with saturated brine, dried on $MgSO_4$ and concentrated. The title product was obtained after flash column chromatography (silica gel, heptane/ethyl acetate (75/25, v/v), $R_f$=0.38), followed by crystallisation from heptane.

Yield: 1.06 g. $^1H$ NMR ($CDCl_3$): δ=10.46 (s, 1H), 7.54 (dd, 1H), 7.35 (t, 1H), 7.17 (d, 1H), 3.96 (s, 3H).

b) 2-Chloro-1-chloromethyl-3-methoxybenzene

At 0° C. a solution of the product of step a (1.00 g) in 5 mL of tetrahydrofuran was added to a suspension of lithium aluminium hydride (0.34 g) in 5 mL of tetrahydrofuran. The reaction mixture was stirred at room temperature for 1 h and water (0.35 mL) in 5 mL tetrahydrofuran was added at 0° C., followed by 2 M sodium hydroxide in water (0.70 mL) and water (0.70 mL). The obtained white suspension was stirred for 0.5 h. and filtered. The colourless oil obtained after concentration of the filtrate was dissolved in 10 mL of 1,2-dichloropropane and thionyl chloride (1.5 mL) was added. The reaction mixture was refluxed overnight and concentrated. The title compound was obtained after flash column chromatography (silica gel, heptane/ethyl acetate (75/25, v/v), $R_f$=0.43) as a yellow oil, that crystallised on standing.

Yield: 0.80 g. $^1$H NMR (CDCl$_3$): δ=7.24 (t, 1H), 7.09 (dd, 1H), 6.93 (dd, 1H), 4.72 (s, 2H), 3.92 (s, 3H).

c) 3-Bromo-4-(2-chloro-3-methoxybenzyloxy)-5-ethoxybenzaldehyde

The title compound was obtained analogously to example 15a, starting from the product of step b (0.42 g) and 5-bromo-3-ethoxy-4-hydroxybenzaldehyde (0.49 g).

Yield: 0.56 g. $^1$H NMR (CDCl$_3$): δ=9.85 (s, 1H), 7.66 (dd, 1H), 7.40 (dd, 1H), 7.39 (d, 1H), 7.29 (t, 1H), 6.94 (dd, 1H), 5.32 (s, 2H), 4.15 (quar., 2H), 3.93 (s, 3H), 1.44 (t, 3H).

d) 4-[3-Bromo-4-(2-chloro-3-methoxybenzyloxy)-5-ethoxyphenyl]-2-methyl-5-oxo-7-propyl-1,4,5,6,7,8-hexahydroquinoline-3-carbonitrile The title compound was obtained analogously to example 1a, starting from 5-propylcyclohexane-1,3-dione (21 mg) and the product of step c (53 mg).

Yield: 60 mg. $R_f$ (heptane/ethyl acetate (4/6, v/v))=0.19. MS-ESI: [M−H]$^−$=597/599/601.

Example 24

Glycine N-3-[2-bromo-4-(3-cyano-2-methyl-5-oxo-7-propyl-1,4,5,6,7,8-hexahydroquinolin-4-yl)-6-ethoxyphenoxymethyl]benzoyl methyl ester a) 3-[2-Bromo-4-(3-cyano-2-methyl-5-oxo-7-propyl-1,4,5,6,7,8-hexahydroquinolin-4-yl)-6-ethoxyphenoxymethyl]-benzoic acid methyl ester The title compound was obtained analogously to example 1a, starting from 5-propylcyclohexane-1,3-dione (0.95 g) and the product of example 15a (2.4 g).

Yield: 3.0 g. $R_f$ (heptane/ethyl acetate (1/1, v/v))=0.20. MS-ESI: [M−H]$^−$=591/593.

b) 3-[2-Bromo-4-(3-cyano-2-methyl-5-oxo-7-propyl-1,4,5,6,7,8-hexahydroquiolin-4-yl)-6-ethoxyphenoxymethyl]-benzoic acid The title compound was obtained analogously to example 13b, starting from the product of step a (3.0 g).

Yield: 3.0 g. MS-ESI: [M−H]$^−$=577/579.

c) Glycine, N-3-[2-bromo-4-(3-cyano-2-methyl-5-oxo-7-propyl-1,4,5,6,7,8-hexahydroquinolin-4-yl)-6-ethoxyphenoxymethyl]benzoyl methyl ester The title compound was obtained analogously to example 14, starting from the product of step b (90 mg) and glycine methyl ester hydrochloride (64 mg). Purification was accomplished via preparative HPLC (Luna C18 [5 μm], flow: 20 ml min$^{-1}$, 0→90% CH$_3$CN, 1% TFA).

Yield: 59 mg. $R_f$ (CH$_2$Cl$_2$/MeOH (95/5, v/v))=0.54. MS-ESI: [M+H]$^+$=650/652.

Example 25

4-[3-Bromo-5-ethoxy-4-(3-methoxybenzyloxy)-phenyl]-7-(4-chlorophenyl)-2-methyl-5-oxo-1,4,5,6,7,8-hexahydroquinoline-3-carbonitrile a) 3-Bromo-5-ethoxy-4-(3-methoxybenzyloxy)-benzaldehyde The title compound was obtained analogously to example 15a, starting from 3-bromo-5-ethoxy-4-hydroxybenzaldehyde (0.75 g) and 1-bromomethyl-3-methoxybenzene (0.48 mL).

Yield: 0.91 g. $R_f$ (heptane/ethyl acetate (2/1, v/v))=0.43. $^1$H NMR (CDCl$_3$): δ=9.83 (s, 1H), 7.65 (dd, 1H), 7.38 (dd, 1H), 7.29 (t, 1H), 7.13 (bs, 1H), 7.07 (d, 1H), 6.88 (dd, 1H), 5.16 (s, 2H), 4.16 (quar., 2H), 3.83 (s, 3H), 1.56 (t, 3H).

b) 4-[3-Bromo-5-ethoxy-4-(3-methoxybenzyloxy)-phenyl]-7-(4-chlorophenyl)-2-methyl-5-oxo-1,4,5,6,7,8-hexahydroquinoline-3-carbonitrile The title compound was obtained analogously to example 1a, starting from 5-(4-chlorophenyl)-cyclohexane-1,3-dione (22 mg) and the product of step a (37 mg).

Yield: 32 mg. $R_f$ (heptane/ethyl acetate (3/7, v/v))=0.19. MS-ESI: [M+H]$^+$=633/635/637.

Example 26

4-[3-Bromo-5-ethoxy-4-(3-methoxybenzyloxy)-phenyl]-7-furan-2-yl-2-methyl-5-oxo-1,4,5,6,7,8-hexahydroquinoline-3-carbonitrile The title compound was obtained analogously to example 1a, starting from 5-furan-2-ylcyclohexane-1,3-dione (18 mg) and the product of example 25a (37 mg).

Yield: 37 mg. $R_f$ (heptane/ethyl acetate (3/7, v/v))=0.24. MS-ESI: [M+H]$^+$=589/591.

Example 27

4-[3,5-Dimethoxy-4-(3-methoxybenzyloxy)-phenyl]-2-methyl-5-oxo-7-propyl-1,4,5,6,7,8-hexahydroquinoline-3-carbonitrile a) 3,5-Dimethoxy-4-(3-methoxybenzyloxy)-benzaldehyde The title compound was obtained analogously to example 15a, starting from 4-hydroxy-3,5-dimethoxybenzaldehyde (0.91 g) and 1-bromomethyl-3-methoxybenzene (0.75 mL).

Yield: 1.42 g light-yellow oil. $R_f$ (heptane/ethyl acetate (1/1, v/v))=0.40. $^1$H NMR (CDCl$_3$): δ=9.86 (s, 1H), 7.26 (d, 1H), 7.23 (d, 1H), 7.09 (bs, 1H), 7.04 (d, 1H), 6.85 (dd, 1H), 5.12 (s, 2H), 3.91 (s, 6H), 3.82 (s, 3H).

b) 4-[3,5-Dimethoxy-4-(3-methoxybenzyloxy)-phenyl]-2-methyl-5-oxo-7-propyl-1,4,5,6,7,8-hexahydroquinoline-3-carbonitrile The title product was obtained analogously to example 1a, starting from 5-propylcyclohexane-1,3-dione (11 mg) and the product of step a (21 mg).

Yield: 22 mg. $R_f$ (heptane/ethyl acetate (3/7, v/v))=0.21. MS-ESI: [M+H]$^+$=503; [M+Na]$^+$=525.

Example 28

4-[3-Bromo-5-ethoxy-4-(3-pyridinylmethoxy)phenyl]-2-methyl-5-oxo-7-propyl-1,4,5,6,7,8-hexahydroquinoline-3-carbonitrile trifluoroacetic acid a) 3-Bromo-5-ethoxy-4-(3-pyridinylmethoxy)-benzaldehyde The title compound was obtained analogously to example 15a, starting from 3-bromo-5-ethoxy-4-hydroxybenzaldehyde (0.25 g) and 3-picolyl chloride hydrochloride (0.16 g).

b) 4-[3-Bromo-5-ethoxy-4-(3-pyridinylmethoxy) phenyl]-2-methyl-5-oxo-7-propyl-1,4,5,6,7,8-hexahydroquinoline-3-carbonitrile trifluoroacetic acid The title compound was obtained analogously to example 1a, starting from 5-propylcyclohexane-1,3-dione (0.15 g) and the crude product of step a. The compound was purified by semi-preparative HPLC (Luna C18 [5 μm], flow: 20 ml min$^{-1}$, 10→90% CH$_3$CN, 0.1% TFA) and freeze-dried from a mixture of water and dioxane.
Yield: 0.25 g. MS-ESI: [M+H]$^+$=536/538.

Example 29

4-[2-Bromo-4-(3-cyano-2-methyl-5-oxo-7-propyl-1,4,5,6,7,8-hexahydroquinolin-4-yl)-6-ethoxyphenoxymethyl]-N-thiophen-2-ylmethylbenzamide a) 4-(2-Bromo-6-ethoxy-4-formylphenoxymethyl)-benzoic acid methyl ester The title compound was obtained analogously to example 15a, starting from 4-bromomethylbenzoic acid methyl ester (3.7 g).
Yield: 6.4 g. $^1$H NMR (CDCl$_3$): δ=9.84 (s, 1H), 8.06 (d, 2H), 7.65 (d, 1H), 7.61 (d, 2H), 7.39 (d, 1H), 5.03 (s, 2H), 4.16 (q, 2H), 3.93 (s, 3H), 1.48 (t, 3H).

b) 4-[2-Bromo-4-(3-cyano-2-methyl-5-oxo-7-propyl-1,4,5,6,7,8-hexahydroquinolin-4-yl)-6-ethoxyphenoxymethyl]-benzoic acid methyl ester The title compound was obtained analogously to example 1a, starting from 5-propylcyclohexane-1,3-dione (2.5 g) and the product of step a (6.4 g).
Yield: 6.7 g. $R_f$ (heptane/ethyl acetate (3/2, v/v))=0.20. MS-ESI: [M−H]$^−$=591/593.

c) 4-[2-Bromo-4-(3-cyano-2-methyl-5-oxo-7-propyl-1,4,5,6,7,8-hexahydroquinolin-4-yl)-6-ethoxyphenoxymethyl]-benzoic acid The title compound was obtained analogously to example 13b, starting from the product of step b (6.7 g). The reaction mixture was stirred overnight at 50° C.
Yield: 6.4 g. MS-ESI: [M−H]$^−$=577/579.

d) 4-[2-Bromo-4-(3-cyano-2-methyl-5-oxo-7-propyl-1,4,5,6,7,8-hexahydroquinolin-4-yl)-6-ethoxyphenoxymethyl]-N-thiophen-2-ylmethylbenzamide The title compound was obtained analogously to example 14, starting from the product of step c (0.10 g) and 2-thiophenemethylamine (52 μL). Purification was accomplished is via preparative HPLC (Luna C18 [5 μm], flow: 20 ml min$^{-1}$, 10→90% CH$_3$CN, 1% TFA).
Yield: 54 mg. MS-ESI: [M+H]$^+$=674/676.

Example 30

4-[3-Bromo-5-ethoxy-4-(4-nitrophenoxy-phenyl]-2-methyl-5-oxo-7-propyl-1,4,5,6,7,8-hexahydroquinoline-3-carbonitrile a) 4-(3-Bromo-4-hydroxy-5-ethoxyphenyl)-2-methyl-5-oxo-7-propyl-1,4,5,6,7,8-hexahydroquinoline-3-carbonitrile The title compound was obtained analogously to example 1a, starting from 3-bromo-5-ethoxy-4-hydroxybenzaldehyde (2.0 g) and 5-propylcyclohexane-1,3-dione (1.3 g).
Yield: 3.6 g. MS-ESI: [M−H]$^−$=443/445.

b) 4-(3-Bromo-4-mesyloxy-5-ethoxyphenyl)-2-methyl-5-oxo-7-propyl-1,4,5,6,7,8-hexahydroquinoline-3-carbonitrile A mixture of the crude product of step a (0.99 g), mesyl chloride (0.46 mL) and sodium hydroxide 0.32 g) in 4 mL of THF/water (1/1, v/v) was stirred at room temperature for 3 days. Water was added and the reaction mixture was extracted with dichloromethane. Crude title compound was obtained after concentration of the organic phases.
Yield: 1.0 g. MS-ESI: [M−H]$^−$=521/523.

c) 4-[3-Bromo-5-ethoxy-4-(4-nitrophenoxy)-phenyl]-2-methyl-5-oxo-7-propyl-1,4,5,6,7,8-hexahydroquinoline-3-carbonitrile A mixture of the product of step b (0.20 g), 1-fluoro-4-nitrobenzene (53 μL) and cesium carbonate (0.22 g) was dissolved in dimethyl sulfoxide (1 mL) and stirred at 80° C. for 16 h. Dichloromethane was added and the reaction mixture was washed with a solution of 1% hydrochloric acid in water and with saturated brine. The organic phase was concentrated and the title compound was obtained after flash column chromatography (silica gel, heptane/ethyl acetate).
Yield: 0.19 g. MS-ESI: [M−H]$^−$=564/566. $^1$H NMR (CDCl$_3$): δ=8.17 (d, 2H), 7.00 (d, 1H), 6.91 (m, 3H), 5.95 (bs, 1H), 4.63 (s, 1H), 4.04 (dq, 2H), 2.52 (dd, 1H), 2.42 (d, 2H), 2.25 (m, 1H), 2.20 (s, 3H), 2.15 (dd, 1H), 1.38 (m, 4H), 1.20 (t, 3H), 0.92 (t, 3H).

Example 31

4-[3-Bromo-5-ethoxy-4-(5-fluoro-2-propylamino-benzyloxy)-phenyl]-2-methyl-5-oxo-7-propyl-1,4,5,6,7,8-hexahydro-quinoline-3-carbonitrile a) (5-Fluoro-2-nitro-phenyl)-methanol To a solution of 5-fluoro-2-nitrobenzoic acid (4.58 g) in THF (50 ml) was added a 1 M solution of BH$_3$.THF in THF (62 ml) while cooling with an ice-bath. The cooling bath was removed and stirring was continued for 1 h at ambient temperature, followed by refluxing for 4 h. The reaction mixture was cooled and MeOH was added to destroy the excess of borane. The mixture was concentrated and water and ethyl acetate were added to the residue. The organic layer was washed with brine, dried and concentrated. Yield: 4.3 g.

b) 4-[3-Bromo-5-ethoxy-4-(5-fluoro-2-nitro-benzyloxy)-phenyl]-2-methyl-5-oxo-7-propyl-1,4,5,6,7,8-hexahydro-quinoline-3-carbonitrile A mixture of the crude product of step a (1.5 g), thionyl chloride (1.94 ml) and a few drops of DMF in dichloromethane (30 ml) was stirred for 72 h. The mixture was concentrated in vacuo and the residue was dissolved in DMF (20 ml). To the remaining solution was added the compound described in example 30a (3.9 g), $K_2CO_3$ (6.1 g) and a small amount of tetra-n-butylammonium bromide (ca 50 mg). The mixture was stirred at 60° C. for 5 h. Water and ethyl acetate were added, and the aqueous layer was extracted with ethyl acetate. The combined organic fractions were washed with brine, dried and concentrated. The residue was recrystallized from toluene.

Yield: 3.8 g c) 4-[4-(2-Amino-5-fluoro-benzyloxy)-3-bromo-5-ethoxy-phenyl]-2-methyl-5-oxo-7-propyl-1,4,5,6,7,8-hexahydro-quinoline-3-carbonitrile To a solution of the product of step b (3.8 g) in THF (110 ml) were added acetic acid (3.6 ml) and zinc dust (8.2 g). The suspension was heated for 1 h at 50° C. The reaction mixture was filtered and concentrated. The residue was dissolved in ethyl acetate and washed with sat. $NaHCO_3$ and brine. The organic layer was separated, dried ($Na_2SO_4$) and concentrated. The remaining solid was stirred with a small amount of ethyl acetate to give the title compound as a pale yellow solid after filtration.

Yield: 2.8 g d) 4-[3-Bromo-5-ethoxy-4-(5-fluoro-2-propylamino-benzyloxy)-phenyl]-2-methyl-5-oxo-7-propyl-1,4,5,6,7,8-hexahydro-quinoline-3-carbonitrile A solution of the compound described in step c (200 mg) and propionaldehyde (25 μl) in dichloromethane (5 ml) was stirred for 2 h. Then, acetic acid (81 μl) and sodium triacetoxyborohydride (300 mg) were added and the mixture was stirred for an additional 20 h. A 2 M aqueous NaOH solution was added and stirring was continued for 15 min. The organic layer was washed with water and brine, dried and concentrated in vacuo. The title compound was obtained by purification of the residue by preparative HPLC (Luna C18 [5 μm], flow: 20 ml min$^{-1}$, 10→90% $CH_3CN$, 0.1% TFA) and freeze-drying from a mixture of water and dioxane. Some di-alkylated product could be isolated as well (see example 32).

Yield: 109 mg. MS-ESI: $[M+H]^+=610/612$.

Example 32

4-[3-Bromo-4-(2-dipropylamino-5-fluoro-benzyloxy)-5-ethoxy-phenyl]-2-methyl-5-oxo-7-propyl-1,4,5,6,7,8-hexahydro-quinoline-3-carbonitrile Obtained from the reaction mixture of example 31d after preparative HPLC (Luna C18 [5 μm], flow: 20 ml min$^{-1}$, 10→90% $CH_3CN$, 0.1% TFA) and freeze-drying from a mixture of water and dioxane.

Yield: 12 mg. MS-ESI: $[M+H]^+=652/654$.

Example 33

CHO-FSH In Vitro Bioactivity

FSH activity of compounds were tested in Chinese Hamster Ovary (CHO) cells stably transfected with the human FSH receptor and cotransfected with a cAMP responsive element (CRE)/promotor directing the expression of a firefly luciferase reporter gene. Binding of ligand to the Gs-coupled FSH receptor will result in an increase of cAMP, which in turn will induce an increased transactivation of the luciferase reporter construct. The luciferase signal was quantified using a luminescence counter. For test compounds, $EC_{50}$ values (concentration of test compound causing half-maximal (50%) stimulation) were calculated. For that purpose the software program GraphPad PRISM, version 3.0 (GraphPad software Inc., San Diego) was used. Compounds of all examples had an activity ($EC_{50}$) of less than $10^{-5}$ M. The compounds of examples 13, 16, 17, 19-21, 23, 26, 28, 31 and 32 showed an $EC_{50}$ of between $10^{-7}$ and $10^{-9}$ M. The compounds of examples 24 and 29 showed an $EC_{50}$ of less than $10^{-9}$ M.

What is claimed is:
1. A dihydropyridine derivative compound according to Formula I,

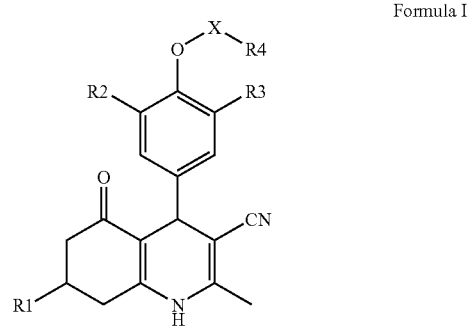

Formula I or a pharmaceutically acceptable salt thereof, wherein
$R^1$ is (1-6C)alkyl, (2-6C)alkenyl, (2-6C)alkynyl or phenyl, (1-5C)heteroaryl, both optionally substituted with one or more substituents selected from hydroxy, amino, halogen, nitro, trifluoromethyl, cyano, (1-4C)alkyl, (2-4C)alkenyl, (2-4C)alkynyl, (1-4C)alkoxy, (1-4C)(di)alkylamino;
$R^2$, $R^3$ are independently (1-4C)alkyl, (2-4C)alkenyl, (2-4C)alkynyl, (1-4C)alkoxy, (2-4C)alkenyloxy, (3-4C)alkynyloxy, halogen;
$R^4$ is (1-6C)alkyl, (2-6C)alkenyl, (2-6C)alkynyl, (3-6C)cycloalkyl, (3-6C)cycloalkenyl, (3-6C)cycloalkyl(1-4C)alkyl, (2-6C)heterocycloalkyl, (2-6C)heterocycloalkyl(1-4C)alkyl or (6-10C)aryl, (6-10C)aryl(1-4C)alkyl, (1-9C)heteroaryl, (1-9C)heteroaryl(1-4C)alkyl, the aryl or heteroaryl group optionally substituted with one or more substituents selected from hydroxy, amino, halogen, nitro, trifluoromethyl, cyano, (1-4C)alkyl, (2-4C)alkenyl, (2-4C)alkynyl, (1-4C)alkoxy, (1-4C)(di)alkylamino, and if $R^4$ is phenyl, phenyl may, in addition, optionally be substituted with the substituents provided for under "aryl" and/or one or more substituents selected from (1-4C)alkylthio, (1-4C)alkylsulfonyl, $R^5$-oxycarbonyl, $R^5$-carbonyl or $R^5$,$R^6$-aminocarbonyl;
X is $SO_2$, $CH_2$, $C(O)$ or X is absent, wherein if X is $CH_2$, $R^4$ may furthermore be $R^5$-oxycarbonyl or $R^5$-carbonyl;

R⁵, R⁶ is independently H, (1-4C)alkyl, (2-4C)alkenyl, (2-4C)alkynyl, (3-6C)cycloalkyl, (3-6C)cycloalkyl(1-4C)alkyl, (2-6C)heterocycloalkyl, (2-6C)heterocycloalkyl(1-4C)alkyl, (1-4C)alkoxycarbonyl(1-4C)alkyl, (1-4C)(di)alkylaminocarbonyl(1-4C)alkyl or (6-10C)arylaminocarbonyl(1-4C)alkyl, (1-9C)heteroarylaminocarbonyl(1-4C)alkyl, (6-10C)aryl, (1-9C)heteroaryl, (6-10C)aryl(1-4C)alkyl, (1-9C)heteroaryl(1-4C)alkyl, the aryl or heteroaryl group optionally substituted with one or more substituents selected from hydroxy, amino, halogen, nitro, trifluoromethyl, cyano, (1-4C)alkyl, (2-4C)alkenyl, (2-4C)alkynyl, (1-4C)alkoxy, (1-4C)(di)alkylamino or R⁵, R⁶ in R⁵, R⁶-aminocarbonyl may be joined in a (2-6C) heterocycloalkyl ring;

wherein (1-9C)heteroaryl is selected from the group consisting of tetrazolyl, imidazolyl, thiadiazolyl, pyridinyl, (benzo)thienyl, (benzo)furyl, (iso)quinolinyl, tetrahydro(iso)quinolinyl, coumarinyl, quinoxalinyl and indolyl;

with the proviso that the compound is not 2-methyl-5-oxo-7-phenyl-4-(3,4,5-trimethoxyphenyl)-1,4,5,6,7,8-hexahydroquinoline-3-carbonitrile.

2. The compound according to claim 1 wherein R⁴ is phenyl optionally substituted with one or more substituents selected from hydroxy, amino, halogen, nitro, trifluoromethyl, cyano, (1-4C)alkyl, (2-4C)alkenyl, (2-4C)alkynyl, (1-4C)alkoxy, (1-4C)(di)alkylamino, (1-4C)alkylthio, (1-4C)alkylsulfonyl, R⁵-oxycarbonyl, R⁵-carbonyl or R⁵,R⁶-aminocarbonyl.

3. The compound according to claim 2 wherein the substituent of phenyl at R⁴ is R⁵, R⁶-aminocarbonyl, (1-4C)alkoxy and/or halogen.

4. The compound according to claim 3 wherein R⁵, R⁶ in R⁵,R⁶-aminocarbonyl is (1-4C)(di)alkylamino.

5. The compound according to claim 3 wherein R⁵ in R⁵,R⁶-aminocarbonyl is (1-4C)alkoxycarbonyl(1-4C)alkyl and R⁶ is H.

6. The compound according to claim 3 wherein R⁵ in R⁵,R⁶ aminocarbonyl is (1-9C)heteroaryl(1-4C)alkyl, the aryl or heteroaryl group optionally substituted with one or more substituents selected from hydroxy, amino, halogen, nitro, trifluoromethyl, cyano, (1-4C)alkyl, (2-4C)alkenyl, (2-4C)alkynyl, (1-4C)alkoxy, (1-4C)(di)alkylamino or (1-4C)alkoxycarbonyl(1-4C)alkyl and R⁶ is H.

7. The compound according to claim 1 wherein X is $CH_2$.

8. The compound according to claim 1 wherein R¹ is (1-6C) alkyl, phenyl or (1-5C)heteroaryl.

9. The compound according to claim 1 wherein R², R³ are halogen and/or (1-4C)alkoxy.

10. A pharmaceutical composition comprising the compound according to Formula I,

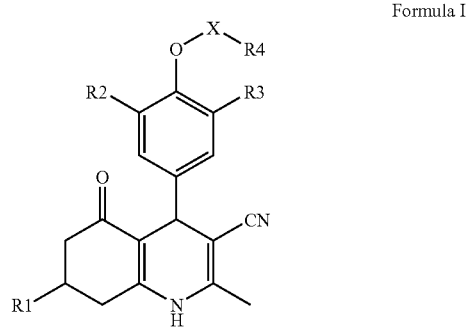

Formula I or a pharmaceutically acceptable salt thereof, wherein
R¹ is (1-6C)alkyl, (2-6C)alkenyl, (2-6C)alkynyl or phenyl, (1-5C)heteroaryl, both optionally substituted with one or more substituents selected from hydroxy, amino, halogen, nitro, trifluoromethyl, cyano, (1-4C)alkyl, (2-4C)alkenyl, (2-4C)alkynyl, (1-4C)alkoxy, (1-4C)(di)alkylamino;

R², R³ are independently (1-4C)alkyl, (2-4C)alkenyl, (2-4C)alkynyl, (1-4C)alkoxy, (2-4C)alkenyloxy, (3-4C)alkynyloxy, halogen;

R⁴ is (1-6C)alkyl, (2-6C)alkenyl, (2-6C)alkynyl, (3-6C)cycloalkyl, (3-6C)cycloalkenyl, (3-6C)cycloalkyl(1-4C)alkyl, (2-6C)heterocycloalkyl, (2-6C)heterocycloalkyl(1-4C)alkyl or (6-10C)aryl, (6-10C)aryl(1-4C)alkyl, (1-9C)heteroaryl, (1-9C)heteroaryl(1-4C)alkyl, the aryl or heteroaryl group optionally substituted with one or more substituents selected from hydroxy, amino, halogen, nitro, trifluoromethyl, cyano, (1-4C)alkyl, (2-4C)alkenyl, (2-4C)alkynyl, (1-4C)alkoxy, (1-4C)(di)alkylamino, and if R⁴ is phenyl, phenyl may, in addition, optionally be substituted with the substituents provided for under "aryl" and/or one or more substituents selected from (1-4C)alkylthio, (1-4C)alkylsulfonyl, R⁵-oxycarbonyl, R⁵-carbonyl or R⁵,R⁶-aminocarbonyl;

X is $SO_2$, $CH_2$, C(O) or X is absent, wherein if X is $CH_2$, R⁴ may furthermore be R⁵-oxycarbonyl or R⁵-carbonyl;

R⁵, R⁶ is independently H, (1-4C)alkyl, (2-4C)alkenyl, (2-4C)alkynyl, (3-6C)cycloalkyl, (3-6C)cycloalkyl(1-4C)alkyl, (2-6C)heterocycloalkyl, (2-6C)heterocycloalkyl(1-4C)alkyl, (1-4C)alkoxycarbonyl(1-4C)alkyl, (1-4C)(di)alkylaminocarbonyl(1-4C)alkyl or (6-10C)arylaminocarbonyl(1-4C)alkyl, (1-9C)heteroarylaminocarbonyl(1-4C)alkyl, (6-10C)aryl, (1-9C)heteroaryl, (6-10C)aryl(1-4C)alkyl, (1-9C)heteroaryl(1-4C)alkyl, the aryl or heteroaryl group optionally substituted with one or more substituents selected from hydroxy, amino, halogen, nitro, trifluoromethyl, cyano, (1-4C)alkyl, (2-4C)alkenyl, (2-4C)alkynyl, (1-4C)alkoxy, (1-4C)(di)alkylamino or R⁵, R⁶ in R⁵,R⁶-aminocarbonyl may be joined in a (2-6C) heterocycloalkyl ring, and pharmaceutically suitable auxiliaries;

wherein (1-9C)heteroaryl is selected from the group consisting of tetrazolyl, imidazolyl, thiadiazolyl, pyridinyl, (benzo)thienyl, (benzo)furyl, (iso)quinolinyl, tetrahydro(iso)quinolinyl, coumarinyl, quinoxalinyl and indolyl.

11. A method of treating hypogonadism in a patient, the method comprising administering to the patient an effective amount of the compound according to Formula I,

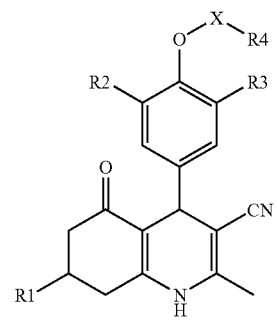

Formula I or a pharmaceutically acceptable salt thereof, wherein
R¹ is (1-6C)alkyl, (2-6C)alkenyl, (2-6C)alkynyl or phenyl, (1-5C)heteroaryl, both optionally substituted with one or more substituents selected from hydroxy, amino, halogen, nitro, trifluoromethyl, cyano, (1-4C)alkyl, (2-4C)alkenyl, (2-4C)alkynyl, (1-4C)alkoxy, (1-4C)(di)alkylamino;

$R^2$, $R^3$ are independently (1-4C)alkyl, (2-4C)alkenyl, (2-4C)alkynyl, (1-4C)alkoxy, (2-4C)alkenyloxy, (3-4C)alkynyloxy, halogen;

$R^4$ is (1-6C)alkyl, (2-6C)alkenyl, (2-6C)alkynyl, (3-6C)cycloalkyl, (3-6C)cycloalkenyl, (3-6C)cycloalkyl(1-4C)alkyl, (2-6C)heterocycloalkyl, (2-6C)heterocycloalkyl(1-4C)alkyl or (6-10C)aryl, (6-10C)aryl(1-4C)alkyl, (1-9C)heteroaryl, (1-9C)heteroaryl(1-4C)alkyl, the aryl or heteroaryl group optionally substituted with one or more substituents selected from hydroxy, amino, halogen, nitro, trifluoromethyl, cyano, (1-4C)alkyl, (2-4C)alkenyl, (2-4C)alkynyl, (1-4C)alkoxy, (1-4C)(di)alkylamino, and if $R^4$ is phenyl in addition with (1-4C)alkylthio, (1-4C)alkylsulfonyl, $R^5$-oxycarbonyl, $R^5$-carbonyl or $R^5,R^6$-aminocarbonyl;

X is $SO_2$, $CH_2$, $C(O)$ or X is absent, wherein if X is $CH_2$, $R^4$ may furthermore be $R^5$-oxycarbonyl or $R^5$-carbonyl;

$R^5$, $R^6$ is independently H, (1-4C)alkyl, (2-4C)alkenyl, (2-4C)alkynyl, (3-6C)cycloalkyl, (3-6C)cycloalkyl(1-4C)alkyl, (2-6C)heterocycloalkyl, (2-6C)heterocycloalkyl(1-4C)alkyl, (1-4C)alkoxycarbonyl(1-4C)alkyl, (1-4C)(di)alkylaminocarbonyl(1-4C)alkyl or (6-10C)arylaminocarbonyl(1-4C)alkyl, (1-9C)heteroarylaminocarbonyl(1-4C)alkyl, (6-10C)aryl, (1-9C)heteroaryl, (6-10C)aryl(1-4C)alkyl, (1-9C)heteroaryl(1-4C)alkyl, the aryl or heteroaryl group optionally substituted with one or more substituents selected from hydroxy, amino, halogen, nitro, trifluoromethyl, cyano, (1-4C)alkyl, (2-4C)alkenyl, (2-4C)alkynyl, (1-4C)alkoxy, (1-4C)(di)alkylamino or $R^5$, $R^6$ in $R^5,R^6$-aminocarbonyl may be joined in a (2-6C) heterocycloalkyl ring, wherein (1-9C)heteroaryl is selected from the group consisting of tetrazolyl, imidazolyl, thiadiazolyl, pyridinyl, (benzo)thienyl, (benzo)furyl, (iso)quinolinyl, tetrahydro(iso)quinolinyl, coumarinyl, quinoxalinyl and indolyl.

12. A method for treating infertility in a patient by ovulation induction or by controlled hyperstimulation, wherein the infertility is associated with a fertility disorder which is responsive to FSH receptor mediated pathways, the method comprising administering to the patient an effective amount of the compound according to Formula I,

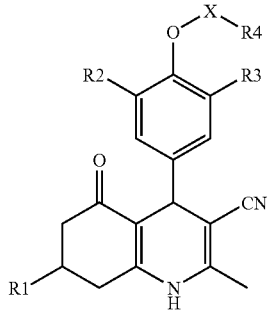

Formula I or a pharmaceutically acceptable salt thereof, wherein
$R^1$ is (1-6C)alkyl, (2-6C)alkenyl, (2-6C)alkynyl or phenyl, (1-5C)heteroaryl, both optionally substituted with one or more substituents selected from hydroxy, amino, halogen, nitro, trifluoromethyl, cyano, (1-4C)alkyl, (2-4C)alkenyl, (2-4C)alkynyl, (1-4C)alkoxy, (1-4C)(di)alkylamino;

$R^2$, $R^3$ are independently (1-4C)alkyl, (2-4C)alkenyl, (2-4C)alkynyl, (1-4C)alkoxy, (2-4C)alkenyloxy, (3-4C)alkynyloxy, halogen;

$R^4$ is (1-6C)alkyl, (2-6C)alkenyl, (2-6C)alkynyl, (3-6C)cycloalkyl, (3-6C)cycloalkenyl, (3-6C)cycloalkyl(1-4C)alkyl, (2-6C)heterocycloalkyl, (2-6C)heterocycloalkyl(1-4C)alkyl or (6-10C)aryl, (6-10C)aryl(1-4C)alkyl, (1-9C)heteroaryl, (1-9C)heteroaryl(1-4C)alkyl, the aryl or heteroaryl group optionally substituted with one or more substituents selected from hydroxy, amino, halogen, nitro, trifluoromethyl, cyano, (1-4C)alkyl, (2-4C)alkenyl, (2-4C)alkynyl, (1-4C)alkoxy, (1-4C)(di)alkylamino, and if $R^4$ is phenyl in addition with (1-4C)alkylthio, (1-4C)alkylsulfonyl, $R^5$-oxycarbonyl, $R^5$-carbonyl or $R^5,R^6$-aminocarbonyl;

X is $SO_2$, $CH_2$, $C(O)$ or X is absent, wherein if X is $CH_2$, $R^4$ may furthermore be $R^5$-oxycarbonyl or $R^5$-carbonyl;

$R^5$, $R^6$ is independently H, (1-4C)alkyl, (2-4C)alkenyl, (2-4C)alkynyl, (3-6C)cycloalkyl, (3-6C)cycloalkyl(1-4C)alkyl, (2-6C)heterocycloalkyl, (2-6C)heterocycloalkyl(1-4C)alkyl, (1-4C)alkoxycarbonyl(1-4C)alkyl, (1-4C)(di)alkylaminocarbonyl(1-4C)alkyl or (6-10C)arylaminocarbonyl(1-4C)alkyl, (1-9C)heteroarylaminocarbonyl(1-4C)alkyl, (6-10C)aryl, (1-9C)heteroaryl, (6-10C)aryl(1-4C)alkyl, (1-9C)heteroaryl(1-4C)alkyl, the aryl or heteroaryl group optionally substituted with one or more substituents selected from hydroxy, amino, halogen, nitro, trifluoromethyl, cyano, (1-4C)alkyl, (2-4C)alkenyl, (2-4C)alkynyl, (1-4C)alkoxy, (1-4C)(di)alkylamino or $R^5$, $R^6$ in $R^5,R^6$-aminocarbonyl may be joined in a (2-6C) heterocycloalkyl ring, wherein (1-9C)heteroaryl is selected from the group consisting of tetrazolyl, imidazolyl, thiadiazolyl, pyridinyl, (benzo)thienyl, (benzo)furyl, (iso)quinolinyl, tetrahydro(iso)quinolinyl, coumarinyl, quinoxalinyl and indolyl.

13. A dihydropyridine derivative compound selected from the group consisting of
3-[2-Bromo-4-(3-cyano-2-methyl-5-oxo-7-phenyl-1,4,5,6,7,8-hexahydroquinolin-4-yl)-6-methoxyphenoxymethyl]-N-thiophen-2-ylmethylbenzamide;
  Glycine, N-3-[2-bromo-4-(3-cyano-2-methyl-5-oxo-7-phenyl-1,4,5,6,7,8-hexahydroquinolin-4-yl)-6-ethoxyphenoxymethyl]benzoyl, methyl ester;
  3-[2-Bromo-4-(3-cyano-7-ethyl-2-methyl-5-oxo-1,4,5,6,7,8-hexahydroquinolin-4-yl)-6-ethoxyphenoxymethyl]-benzoic acid methyl ester;
  3-[2-Bromo-4-(3-cyano-7-ethyl-2-methyl-5-oxo-1,4,5,6,7,8-hexahydroquinolin-4-yl)-6-ethoxyphenoxymethyl]- N-tert-butylbenzamide;
  3-[2-Bromo-4-(3-cyano-7-ethyl-2-methyl-5-oxo-1,4,5,6,7,8-hexahydroquinolin-4-yl)-6-ethoxyphenoxymethyl]-N-cyclohexylbenzamide;
  3-[2-Bromo-4-(3-cyano-7-ethyl-2-methyl-5-oxo-1,4,5,6,7,8-hexahydroquinolin-4-yl)-6-ethoxyphenoxymethyl]-N-(2-morpholin-4-yl-ethyl)-benzamide;
  4-[3-Bromo-4-(2-chloro-3-methoxybenzyloxy)-5-ethoxyphenyl]-2-methyl-5-oxo-7-propyl-1,4,5,6,7,8-hexahydroquinoline-3-carbonitrile;
  Glycine, N-3-[2-bromo-4-(3-cyano-2-methyl-5-oxo-7-propyl-1,4,5,6,7,8-hexahydroquinolin-4-yl)-6-ethoxyphenoxymethyl]benzoyl, methyl ester;

4-[3-Bromo-5-ethoxy-4-(3-methoxybenzyloxy)-phenyl]-7-furan-2-yl-2-methyl-5-oxo-1,4,5,6,7,8-hexahydro-quinoline-3-carbonitrile;

4-[3-Bromo-5-ethoxy-4-(3-pyridinylmethoxy)phenyl]-2-methyl-5-oxo-7-propyl-1,4,5,6,7,8-hexahydroquinoline-3-carbonitrile trifluoroacetic acid;

4-[2-Bromo-4-(3-cyano-2-methyl-5-oxo-7-propyl-1,4,5,6,7,8-hexahydroquinolin-4-yl)-6-ethoxyphenoxymethyl]-N-thiophen-2-ylmethylbenzamide;

4-[3-Bromo-5-ethoxy-4-(5-fluoro-2-propylamino-benzyloxy)-phenyl]-2-methyl-5-oxo-7-propyl-1,4,5,6,7,8-hexahydro-quinoline-3-carbonitrile; and 4-[3-Bromo-4-(2-dipropylamino-5-fluoro-benzyloxy)-5-ethoxy-phenyl]-2-methyl-5-oxo-7-propyl-1,4,5,6,7,8-hexahydro-quinoline-3-carbonitrile, or a pharmaceutically acceptable salt thereof.

\* \* \* \* \*